United States Patent [19]
Bird et al.

[11] Patent Number: 5,612,471
[45] Date of Patent: Mar. 18, 1997

[54] NEMATODE-INDUCED GENES IN TOMATO

[75] Inventors: David McK. Bird, Riverside; Mark A. Wilson, Moreno Valley, both of Calif.

[73] Assignee: The Regents of the University of California, Oakland, Calif.

[21] Appl. No.: 248,474

[22] Filed: May 25, 1994

[51] Int. Cl.$^6$ .................................................. C12N 15/11
[52] U.S. Cl. ........................................ 536/24.1; 536/23.6
[58] Field of Search ................................. 536/24.1, 23.2, 536/23.6; 435/320.1, 172.3; 800/205, DIG. 44

[56] References Cited

FOREIGN PATENT DOCUMENTS

| | | |
|---|---|---|
| 0517367A1 | 12/1992 | European Pat. Off. . |
| WO9204453 | 3/1992 | WIPO . |
| WO92/15690 | 9/1992 | WIPO . |
| WO92/21757 | 12/1992 | WIPO . |
| WO93/06710 | 4/1993 | WIPO . |
| WO93/10251 | 5/1993 | WIPO . |
| WO93/18170 | 9/1993 | WIPO . |

OTHER PUBLICATIONS

Opperman, et al (14 Jan. 1994) Science 263:221–223.
Wiggers, R.J., et al. (1990) "DNA Content and Variation in Chromosome No. in Plant Cells Affected by *Meloidogyne incognita* and *M. arenaria*", *Phytopathology*, 80(12):1391–1395.
Wiggers, R.J., et al. (1991) "Evidence Against Amplification of Four Genes in Giant Cells Induced by *Meloidogyne incognita*", *Journal of Nematology*, 23(4):421–424.
Burrows, Paul R. (1992) "Molecular Analysis of the Interactions between Cyst Nematodes and Their Hosts", *Journal of Nematology*, 24(3):338–342.
Taylor, C. G., et al. (1992) "Characterization of a nematode-responsive plant gene promoter", *Journal of Nematology*, 24:621.
Yamamoto, Yuri, T., et al. (1991) "Characterization of cis-Acting Sequences Regulating Root–Specific Gene Expression in Tobacco", *The Plant Cell*, 3:371–382.
Hammond–Kosack, Kim E., et al. (1990) "Changes in abundance of translatable mRNA species in potato roots and leave following root invasion by cyst–nematode G. Rostochiensis pathotypes", *Physiological and Molecular Plant Pathhology*, 37:339–354.
Conkling, Mark A., et al. (1990) "Isolation of Transcriptionally Regulated Root–Specific Genes from Tobacco", *Plant Physiol.* 93:1203–1211.
Opperman et al., "Root–Knot Nematode–Directed Expression of a Plant Root–Specific Gene," *Science* (14 Jan. 1994) 263: 221–223.
Goddijn et al., "Analysis of Gene Activity in Nermatode–Induced Feeding Structures, Using Promoter–GUS Fusions and Promoter Tagging," *Journal of Cellular Biochemistry*, Supplement O(18 Part A) (9–16 Jan. 1994) Abstract X1–133 p. 93.
Cramer et al., "Regulation of Defense–Related Gene Expression During Plant–Pathogen Interactions," *Journal of Nematology* (1993) 25(4): 507518.

*Primary Examiner*—Che S. Chereskin
*Attorney, Agent, or Firm*—Townsend and Townsend and Crew

[57] ABSTRACT

The present invention provides nucleic sequences from genes which are preferentially expressed in feeding site cells. These sequences can be used to produce transgenic plants resistant to nematode infection.

1 Claim, 3 Drawing Sheets

FIGURE 2

```
 K  PSSDS
YK  PSYDNS
YKKPSYDSG
YK  PSYDNG
YKKPSYDSG
YK  PSYDS
YK  PSYDN
YK  PSYDS
YK  PSYDN
YK  PSYDRL*

TS  PSYSP
```

FIGURE 3

| | | QLQAKHGNKWRKIAAEVPGRTAKRLGKWWEVSKRRQQREQ |
|---|---|---|
| DB#280: | | |
| Petunia Ph3 | [Z13998] | +L AK  GNKW ++AA++PGRT  +  +W    +R+QR |
| Moss | [S24244] |  L A   GN+W +IAA++PGRT  +  +W    +++ R Q |
| Snapdragon 315 | [JQ0961] | +L A   GN+W KIA  +PGRT  +  +W    +++ |
| Barley HV33 | [P20027] |        GN+W +IA+  +PGRT  +  +W    +++ R+Q |
| Snapdragon 308 | [JQ0960] | +L +   GNKW  IA   +PGRT  +  +W    RR+ |
| Arabidopsis MYB1 | [D10936] |    A HGNKW  IA   +PGRT  +   W  + RR+ |
| Maize Zm.P1 | [P27898] | +L A   GN+W  IA   +PGRT  +  +W     RQ |
| Drosophila | [P04197] |  Q +   GN+W KIA   +PGRT  +   W  + RR+ |
| Human | [M13666] |  Q +   GN+W +IA   +PGRT  +   W  + RR+  ++ |

FIGURE 4

```
Tobacco:  TGACCAGATAAAACAAATTTGTCTCGATAAAGGGGGAAAACTTTTATCTTCTCGTGATCTTCCCCCCATC...
          |||   |||||||||||| ||  ||  |||||||||||||||  ||||||||||| ||| |||||||||
DB#226:   ATAAACAAAAAACATGTCTCTTTAATATAAAGGGGGAAAACATTGTCTTGTGTTGTCTTCCCCCTCTCA Tobacco:  TATTTTACTTAACTTCGTTATGTATTTTGATTTTGAAGCGCCCGCCCATTGAAAGGGAGGATTGTGTCCAA
          ||| || ||||||||||||||| |   | ||   |||      |||||||||    | |||||||||| 
DB#226:   TCTATTCTTTAACTTCGTTATG...TTATATCTTGAAGCACCACCCATTGAA.....AGGGATTGTGTCCAT Tobacco:  GTTTTTTCCAACATTTTAATGGTGAAGTGACATCTCCTTGTAACAACACTACTACTCTTCCAAATTCACCTC
          |||||| ||||||| |||||||||||||||||||||||||||||||| |||   |||||||| ||| |||
DB#226:   GTTTTTCCAAAATTTTAATGGTGAAGTGACATTCCTTGTAACAACAGT..TTTCTTACAATTTCTTCAC Tobacco:  CTCTTTCTTTTTCCTTGTTTTTCATTTGATGAGN(24)-polyA
          ||||||  |||||| ||   |||
DB#226:   CTCTTTTTTTCTTTCTT-polyA
```

NEMATODE-INDUCED GENES IN TOMATO

This invention was made with Government support under Grant No. 89-37263-4355 awarded by the U.S. Department of Agriculture. The Government has certain rights in this invention.

BACKGROUND OF THE INVENTION

The present invention relates to methods and nucleic acid compositions for the production of transgenic plants resistant to nematodes. In particular, it relates to nematode-resistant transgenic plants comprising sequences from nematode-induced genes.

Plant parasitic nematodes significantly affect the productive capability of the world's farmlands. They reduce the yield of the world's forty major food staples and cash crops by an average of 12.3%, with losses substantially higher for some commodities (e.g., 20.6% for tomato). In the U.S. the reduced yields cause losses of $5.8 billion annually.

Especially significant in terms of crop losses are the sedentary endoparasites, cyst nematodes (Globodera spp. and Heterodera spp.) and root-knot nematodes (Meloidogyne spp.). Cyst nematodes generally infect potatoes, soybeans, sugar beets, and wheat. Root-knot nematodes affect over 2,000 species of plants, including most of the major crops in the world.

Root-knot nematodes and cyst nematodes have similar life-cycles. Infection occurs after larvae hatch in the soil, invade the root and migrate intercellularly to the developing vascular cylinder where permanent feeding sites are established. Mature feeding sites are characterized by the presence of multinucleate cells, termed "giant cells" in root-knot nematode infections and "syncytia" in cyst nematode infections. These large, avacuolate cells with extensively remodeled cell walls are metabolically active and serve as the obligate nutritive source for the developing nematode. Giant cell formation, coupled with limited proliferation of nearby pericycle and cortical cells results in the characteristic root-knot gall.

Today, nematode infections are controlled primarily using chemical nematicides. These compounds are generally very toxic and have been suspected of causing environmental damage. These concerns have prompted efforts to find other methods of controlling nematodes in economically important crop plants. The present invention addresses these and other needs.

SUMMARY OF THE INVENTION

The present invention provides isolated polynucleotides isolated from nematode-induced genes. In particular, the sequences of the invention are capable of hybridizing under stringent conditions to a nucleic acid having a sequence selected from the group consisting of SEQ. ID. No. 1 through SEQ. ID. No. 18, SEQ. ID. No. 20 through SEQ. ID. No. 33. SEQ. ID. No. 35 through SEQ. ID. No. 45, and SEQ. ID. No. 47 through SEQ. ID. No. 109. The nematode-induced genes of the invention may be used to provide nematode-responsive promoters in expression cassettes for expression of polypeptides that inhibit infection by nematodes, such as root knot nematodes. A number of polypeptides may be encoded. For instance, the polypeptides may inhibit signal transduction associated with feeding cell formation, they may be antibodies, they may elicit a defense response against plant pathogens, or they may be toxic to plant cells or nematodes.

The expression cassettes may also comprise the nematode-responsive promoter operably linked to polynucleotide which inhibits expression of a nematode-induced gene. In these embodiments, the polynucleotide is typically linked to the promoter in an antisense orientation. The polynucleotide can also be used to transcribe a ribozyme.

The invention further provides nematode-resistant transgenic plants comprising the expression cassettes described above. Methods for conferring nematode resistance on plants are also provided.

Definitions

The term "antisense orientation" refers to the orientation of nucleic acid sequence from a structural gene that is inserted in an expression cassette in an inverted manner with respect to its naturally occurring orientation. When the sequence is double stranded, the strand that is the template strand in the naturally occurring orientation becomes the coding strand, and vice versa.

The term "expression" refers to the transcription and translation of a structural gene so that a protein is synthesized.

A "feeding site cell" is an enlarged cell in a plant root which is induced in response to nematode infection and provides nourishment to the developing nematode. Feeding site cells arising in response to root-knot nematode infections are termed giant cells, while those arising in response to cyst nematode infections are termed syncytia.

A "nematode-induced" gene is one which is preferentially expressed in feeding site cells as compared to surrounding normal root tissue. The gene may be one which is normally expressed in other plant tissues (e.g., leaf, cotyledon, apex, or hypocotyl) and is up-regulated in feeding site cells. Alternatively, the gene may be one that is not normally expressed in other plant tissues, but is expressed only in response to nematode infection.

A "nematode-responsive" promoter is one which drives expression of an operably linked polynucleotide sequence substantially only in feeding site cells. One of skill will recognize that control of gene expression is not always complete and that a nematode-responsive promoter may also drive expression to a small extent in cells other than feeding site cells. Thus, a promoter is considered to be nematode responsive if the level of expression, if any, of the operably linked polynucleotide sequence in cells other than feeding site cells is not sufficient to effectively disrupt cellular function. Thus, for example, if the sequence encodes a protein toxic to plant cells, plant cells other than feeding site cells are not adversely affected by the presence of a construct comprising the promoter and the structural gene because the toxic protein is not present in an amount sufficient to effectively disrupt cellular function.

"Nucleic acids" and "polynucleotides", as used herein, may be DNA or RNA. One of skill will recognize that the sequences from nematode-induced genes used in the methods of the invention need not be identical and may be substantially identical (as defined below) to sequences disclosed here. In particular, where a polynucleotide sequence is transcribed and translated to produce a functional polypeptide, one of skill will recognize that because of codon degeneracy a number of polynucleotide sequences will encode the same polypeptide. Similarly, because amino acid residues share properties with other residues, conservative substitutions of amino acids within a polypeptide may lead to distinct polypeptides with similar or identical function.

The term "operably linked" refers to functional linkage between a promoter and a second sequence, wherein the promoter sequence initiates transcription of RNA corresponding to the second sequence.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), or by inspection. Sequences are typically compared using either BlastN or BlastX with default parameters.

Substantial identity of polynucleotide sequences means that a polynucleotide comprises a sequence that has at least 75% sequence identity, preferably at least 80%, more preferably at least 90% and most preferably at least 95%, Typically, two polypeptides are considered to be substantially identical if at least 40%, preferably at least 60%, more preferably at least 90%, and most preferably at least 95 % are identical or conservative substitutions. Sequences are preferably compared to a reference sequence using GAP using default parameters.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that polynucleotide sequences are substantially identical is if two molecules selectively hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at 65° C. with 0.2XSSC.

The term "plant" includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

A "polypeptide which inhibits nematode infection" is any polypeptide which when present in a cell infected by a nematode prevents formation of a feeding cell and/or development of the nematode. Polypeptides which have this property can act by killing or disabling the infected cell or the nematode itself. Alternatively, the polypeptide may inhibit the activity of proteins and other compounds necessary for feeding cell development. A number of polypeptides which inhibit nematode infection are described below.

The term "promoter" refers to a region of DNA upstream from the structural gene and involved in recognition and binding RNA polymerase and other proteins to initiate transcription. A "plant promoter" is a promoter capable of initiating transcription in plant cells.

The phrase "selectively hybridizing to", refers to a hybridization between a probe and a target sequence in which the probe binds substantially only to the target sequence when the target is in a heterogeneous mixture of polynucleotides and other compounds. Such hybridization is determinative of the presence of the target sequence. Although the probe may bind other unrelated sequences, at least 90%, preferably 95% or more of the hybridization complexes formed are with the target sequence.

The phrase "substantially pure" or "isolated" when referring to a polynucleotide or protein, means a chemical composition which is free of other subcellular components of the organism from which it is derived, e.g., tomato plants. Typically, a compound is substantially pure when at least about 85% or more of a sample exhibits a single polypeptide backbone, or polynucleotide sequence. Minor variants or chemical modifications may typically share the same polypeptide sequence. Depending on the purification procedure, purities of 85%, and preferably over 95% pure are possible. Nucleic acid and protein purity or homogeneity may be indicated by a number of means well known in the art, such as gel electrophoresis and the like.

BRIEF DESCRIPTION OF THE DRAWINGS

FIG. 2 shows the carboxyl terminus domain (CTD) of the deduced DB#117 gene product, aligned to show the heptamer repeat. The asterisk represents the carboxy terminus. In bold below is the canonical heptamer repeat for the CTD of the largest subunit of RNA polymerase II.

FIG. 3 shows the deduced DB#280 gene sequence (bold) aligned with Myb sequences from Petunia, moss, the snapdragon 315 and 308 genes, barley, Arabidopsis, maize, Drosophila, and human. Database accession numbers are in brackets. Identical amino acids are indicated, + represents conservative substitutions. None of the sequences have gaps.

FIG. 4 shows alignment of the DB#226 sequence with the 3'UTR of the tobacco (*Nicotiana plumbaginiflora*) pma-4 gene, which encodes a plasmalemma proton ATPase.

DESCRIPTION OF THE PREFERRED EMBODIMENTS

Figure 1:
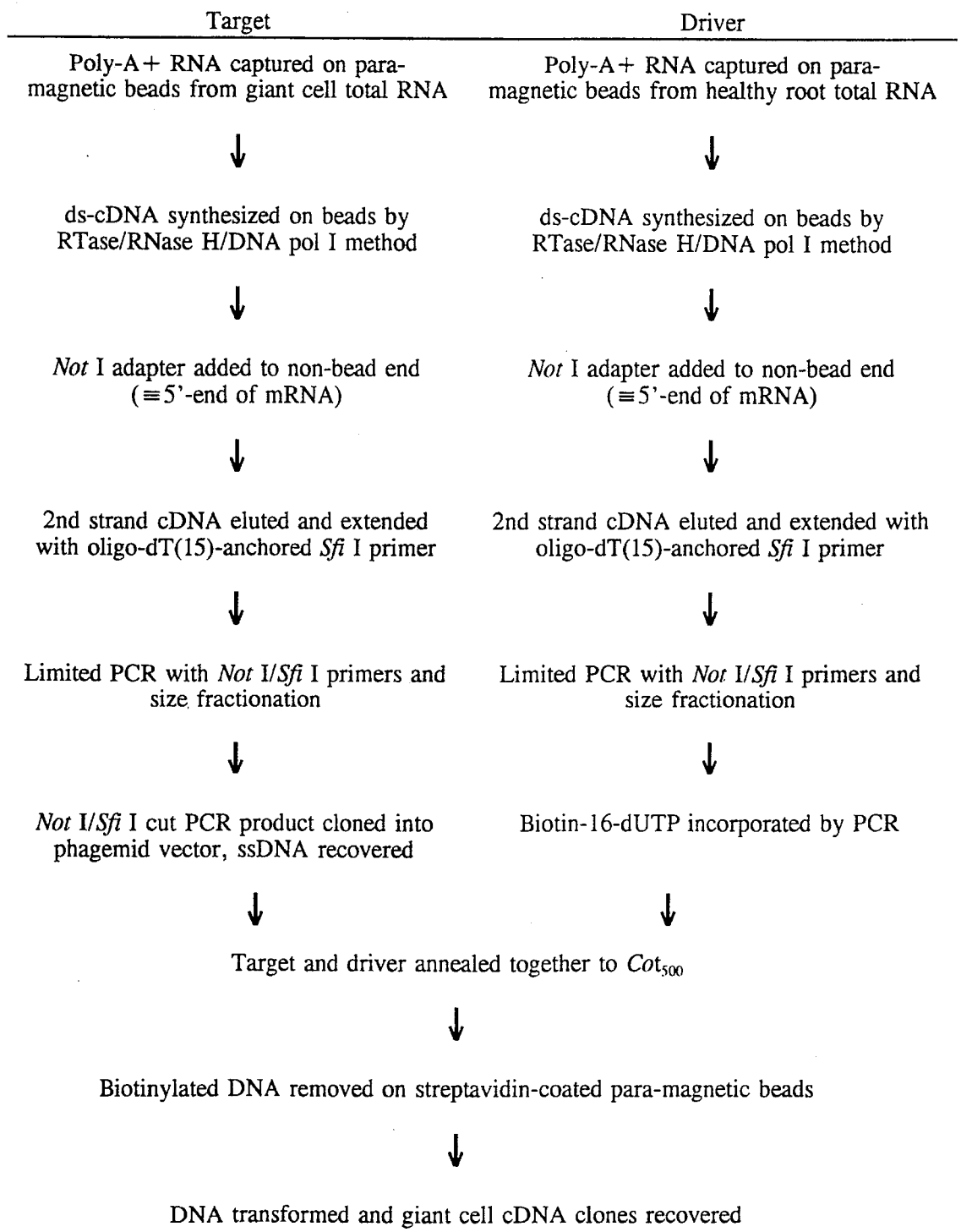
FIG. 1 is a flow diagram outlining the strategy used to construct the cDNA library enriched for nematode-induced sequences.

The invention provides nucleic acid sequences from genes which are preferentially expressed in feeding site cells.

These sequences can be used to produce transgenic plants resistant to nematode infection.

Although feeding site cells, such as giant cells, share features with other plant cells, notably transfer cells, they are a novel cell type, and presumably arise by a pattern of gene expression different from that in other plant cells. It has previously been speculated that gene expression in giant cells might include genes normally expressed at different developmental times or in different cell types (Bird, Mechanisms of the Meloidogyne-host interaction. In: *Nematology: from molecule to ecosystem.* (1992) F. J. Gommers, and P. W. Th. Maas, eds. ESN Inc., Dundee, Scotland).

In a survey of randomly chosen, cloned root mRNAs, Evans et al. (*Mol. Gen. Genet.* 214:153–157 (1988)) were unable to identify any as being root-specific. Using a differential screen, Conkling et al. (*Plant Physiol.* 93:1203–1211 (1990)) isolated genes encoding four, moderately to abundantly expressed, root-specific transcripts from tobacco. The expression of one of these, TobRB7, has been reported to be up-regulated in giant cells induced in tobacco by *Meloidogyne incognita* (Opperman et al. 1994. *Science* 263:221–223). Also using a differential screening approach, Gurr et al. (*Mol. Gen. Genet.* 226:361–366 (1991)) identified a gene in potato whose expression is "correlated with events in the immediate vicinity of the pathogen" (potato cyst nematode, *Globodera rostochiensis*), but the nature of this gene was not revealed.

The present invention is based in part on the isolation of genes whose expression is up-regulated in giant cells as compared to normal root tissue. Although the methods described below relate to the analysis of nematode infected cells, the same approach can be used to identify genes induced by a variety of pathogens (e.g., bacteria, viruses, and fungi) in any crop plant of interest. One of skill will thus recognize that the recombinant DNA techniques for the control of nematodes described below, can also be applied to other pathogens in other crop plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

I. Isolation of nematode-induced genes and nematode-responsive promoters

The isolation of nematode-induced genes from plants may be accomplished by a number of techniques. Such genes are generally isolated using techniques designed to identify sequences specific to a particular tissue or cell types (see, e.g., Sambrook et al. ) Such techniques include differential hybridization techniques as described for instance in Gurr et al. *Mol. Gen. Genet.* 226:361–366 (1991). Briefly, in differential hybridization techniques a cDNA library prepared from feeding site cells is screened with probes generated from cDNA derived from feeding site cells and normal root tissue. Those clones in the cDNA library which show increased hybridization to cDNA from feeding site cells are candidates for genes which are up-regulated in these cells. The clones identified in this way are then used to screen a genomic library to isolate the corresponding gene.

In addition, subtractive hybridization techniques can be used to prepare specific probes for screening cDNA or genomic libraries. These techniques can also be used to prepare subtracted libraries enriched for the desired sequences. Subtractive screening or cDNA cloning approaches have proven effective in identifying transcripts with differential expression profiles. To ensure that cDNAs representing transcripts expressed in low abundance are represented requires that enough cDNA remain after subtraction for efficient cloning. Methods have been developed using PCR and other techniques to ensure that low abundance transcripts are identified. A preferred subtractive hybridization technique using these modifications is described in the Example section, below.

Other techniques for the identification of nematode-induced genes can also be used. For instance, oligonucleotide probes based on the sequences of previously identified nematode-induced genes can be used to isolate the desired gene in a cDNA or genomic DNA library. These techniques can be used to isolate homologous genes in the same or different plant species. The use of such hybridization techniques for identifying homologous genes is well known in the art and need not be described further.

Alternatively, interposon tagging can be used (Topping et al. 1991 *Developm.* 112:1009–1019 and Kertbundit et al. 1991 *Proc. Natl. Acad. Sci. USA* 88:5212–5216). In this method, a number of transgenic plants are produced each carrying a randomly integrated recombinant construct containing a promoterless reporter gene, such as β-glucuronidase (GUS). Various tissues in the plant are then analyzed for expression of the reporter gene. If the reporter gene integrates in a site downstream from a promoter primarily active in a particular tissue, cells in the tissue will contain the reporter gene product. Promoter sequences and genes that are primarily active in feeding site cells can thus be identified.

Once a desired genomic clone is identified, the 5' sequences can be analyzed to identify the promoter sequence from the gene. This can be accomplished using deletion analysis and a promoterless reporter gene (e.g., GUS) to identify those regions which can drive expression of a structural gene.

Sequences characteristic of promoter sequences can also be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983).

In addition, sequence comparison with promoters from other genes that are up-regulated in response to nematode infection can be used to identify regions of sequence homology among the genes. For example, comparison of the 5' flanking sequences of the sequences disclosed here can be used to identify common sequences. Alternatively, other genes previously identified as being nematode-induced (e.g., TobRB7) can be used.

Various methods relying on polymerase chain reaction (PCR) techniques to amplify the desired sequence can also be used. The amplified sequence is then subcloned into a vector where it is then sequenced using standard techniques. For example, PCR can be used to amplify a DNA sequence using a random 5' primer and a defined 3' primer. The 3' primer is based on the sequence of a cDNA isolated by differential screening or subtractive hybridization. The random 5' primer is then used to amplify genomic DNA upstream of the cDNA, to identify promoter sequences. Alternatively, genomic DNA can be cut at a suitable restriction site (determined from Southern blotting experiments) upstream from presumed promoter elements. A linker sequence is attached to the fragments and used as a specific 5' PCR priming site, along with the 3' primer based on the cDNA sequence.

Another approach is to use inverse PCR in which genomic DNA is restricted to generate a sticky ended molecule that spans known sequences at the 5' end of the gene and unknown promoter sequences. The DNA is ligated into circles and PCR amplified with a specific divergent primer pair designed from the cDNA sequence.

II. Production of nematode-resistant plant

Nematode-induced sequences, such as those described here, can be used in a variety of methods using recombinant DNA techniques for the control of nematodes in plants. For instance, the promoters from genes identified here can be used to drive expression of desired sequences in feeding site cells. The sequences can be structural genes encoding desired polypeptides or can be sequences which transcribe RNAs capable of inhibiting the expression of genes required for feeding site cell development. The promoters are used to ensure that the desired sequences are expressed only or substantially only in feeding site cells.

The polypeptides encoded by the structural genes will preferably prevent the development of the nematode in the plant in some way. For instance, the polypeptide may interfere with the transduction of the signal that leads to feeding cell formation in the host. Alternatively, polypeptides which have nematicidal or herbicidal activity can be used. The inhibitory RNAs may function in antisense suppression, sense suppression or as ribzoymes.

A. Construction of expression vectors

The methods required for the recombinant expression of desired genes in transgenic plants are well known to those of skill in the art. Briefly, expression cassettes comprising a promoter from a nematode-induced gene operably linked to desired sequence such as a structural gene encoding a desired protein is introduced into the plant. Construction of appropriate expression vectors is carried out using standard techniques.

The minimal requirements of the vector are that the desired nucleic acid sequence be introduced in a relatively intact state. Thus, any vector which will produce a plant carrying the introduced DNA sequence should be sufficient. The selection of vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press.

The recombinant vectors of the present invention typically comprise an expression cassette designed for initiating transcription of the desired polynucleotide sequences in plants. Companion sequences, of bacterial origin, are also included to allow the vector to be cloned in a bacterial host. The vector will preferably contain a broad host range prokaryote origin of replication. A selectable marker should also be included to allow selection of bacterial cells beating the desired construct. Suitable prokaryotic selectable markers include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

For expression of polypeptides in plants, the recombinant expression cassette will contain, in addition to the desired polynucleotide sequence and the promoter derived from a nematode-induced gene, a transcription initiation site (if the sequence to be transcribed lacks one), and a transcription termination sequence. Unique restriction enzyme sites at the 5' and 3' ends of the cassette are typically included to allow for easy insertion into a pre-existing vector.

The promoters can be modified as necessary to ensure that the desired polynucleotide sequence is expressed substantially only in response to nematode infection. A number of methods can be used to identify those sequences within a given promoter that are responsible for a specific response to nematode infection. As noted above, sequences shared by promoters of nematode-induced genes can be used to design promoters with the desired specificity. Alternatively, a reporter gene (e.g., GUS) can be operably linked to various deletion mutants of the promoter sequence and the ability of the modified promoters to direct expression in feeding site cells and other tissues can be assayed (see, e.g., WO 93/06710).

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

As noted above, an expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet,* 1:419–434, 1982. Polyadenylation sequences include, but are not limited to the Agrobacterium octopine synthase signal (Gielen et at., *EMBO J.,* 3:835–846, 1984) or the nopaline synthase signal (Depicker et at., *Mol. and Appl. Genet,* 1:561–573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

Polypeptides which inhibit nematode infection

As noted above, the promoter can be used to drive expression of structural genes encoding polypeptides which inhibit nematode infection. A variety of structural genes encoding protein or polypeptide products which inhibit the infection by, for instance, inhibiting the process of feeding cell development, promoting a plant defense response, killing or disabling the plant cell, or killing the nematode itself can be used. It is preferred, particularly where the plant is a food plant, that the polypeptide be non-toxic to animals, and particularly be non-toxic to humans.

Polypeptides which inhibit feeding cell formation will typically be competitive inhibitors of the nematode signals which induce feeding cell formation. For instance, proteins encoded by the sequences disclosed here, which are shown to be involved in signal transduction, can used to design highly specific inhibitors of feeding cell formation. In this embodiment of the invention, the polypeptides preferably have sequences substantially identical to those portions of the signal transducing proteins which interact with the appropriate ligand molecule. The signal transducing proteins can also be used to design non-protein inhibitors, which can be used as traditional nematicidal agents.

Genes which produce antibodies immunoreactive with molecules in the plant cell (e.g., proteins, carbohydrates, and nucleic acids) can also be used to inhibit the development of feeding cells (see, e.g., Huse et al., *Science* 246, 1275–1281 (1989)). As used here the term "antibody" refers to a variety of forms of immunoglobulin molecules besides whole antibodies, including for example, Fv, Fab, and F(ab)$_2$ fragments, single chains and the like. Plant proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase. Nematode proteins or nematode-induced molecules can also be targeted. Examples include low molecular weight compounds, with few or no features in common with normal plant products, such as hormones or elements of the signal transduction pathway. Products that play a role in signaling between plants and other organisms (e.g., the nod factor) can also be targeted. Preferred antigens include compounds secreted through the nematode's feeding stylet that initiate and/or maintain feeding cells.

Another class of structural genes which can be used in the invention are those induced by plant pathogens (e.g., nematodes, bacteria, fungi and the like) and that elicit a hypersensitive or other defense responses in plants. Thus, a gene which is normally responsive to a particular pathogen (or to nematodes in another plant species) is made responsive to nematode infection in the transgenic plant. An example of a suitable nematode-inducible gene is the Mi gene from tomato. Examples of suitable genes responsive to other pathogens are reviewed in Stintz et al. *Biochemie* 75:687–706 (1993).

Phytotoxic polypeptides used in the invention may either kill the plant cell in which they are expressed or simply disable the cell so that it is less capable of supporting the pathogen. Examples of suitable structural genes encoding phytotoxic polypeptides include genes encoding enzymes capable of degrading nucleic acids (e.g., nucleases, restriction endonucleases micrococcal nuclease, and ribonucleases such as Rnase A and barnase) and enzymes which attack proteins (e.g., trypsin, pronase A, carboxypeptidase, endoproteinase Asp-N, endoproteinase Glu-C, and endoproteinase Lys-C). Other examples include toxins from plant pathogens (e.g., phaseolotoxin, tabtoxin, and syringotoxin), lipases from porcine pancrease and *Candida cyclindracea*, as well as membrane channel proteins such as glp F and connexins.

Structural genes which are specifically target nematodes include those encoding *Bacillus thuringiensis* toxins as described, for instance, in EP 517, 367 A1. Other proteins include proteinase inhibitors such as cowpea trypsin inhibitor as described in WO 92/15690 or proteins which affect nematode sensory behavior such as miraculin.

Sequences which inhibit expression of nematode-induced genes

Recombinant techniques can also be used to inhibit expression of particular genes which are required for development of feeding site cells. In these techniques inhibitory RNAs (i.e., those which inhibit the expression of target genes) are transcribed in feeding site cells. Promoters from nematode-induced genes are preferably used to direct transcription of the inhibitory RNA sequences only in feeding site cells and thus prevent development of the pathogen. If the target gene is expressed only in feeding site cells, other constitutive or inducible promoters well known to those of skill in the art can also be used. For instance, the 35S promoter from cauliflower mosaic virus may be used. Alternatively, inducible promoters which direct expression only in root tissue can be used.

In some embodiments, antisense regulation of the gene can be used. To accomplish this, a polynucleotide sequence from the desired gene is cloned and operably linked to a promoter (e.g., a promoter from a nematode-induced gene) such that the anti-sense strand of RNA will be transcribed. The construct is then transformed into plants and the antisense strand of RNA is produced. In plant cells, it has been shown that anti-sense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

In other embodiments, cloned polynucleotide sequences configured such that the sense-strand of RNA is produced can be used to block the transcription of target genes in plants. For an example of the use of this method to modulate expression of endogenous genes see, Napoli et at., *The Plant Cell* 2:279–289 (1990), and U.S. Pat. No. 5,034,323.

A third approach is the use of catalytic RNA molecules or ribozymes. Ribozymes can be designed to specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified in the literature. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. Analysis of the self-cleaving RNAs reveals the presence of a conserved regions necessary for cleavage and allows the design of ribozymes specific for a target RNA. The design and use of target RNA-specific ribozymes is described in Haseloff et al. *Nature,* 334:585–591 (1988).

The inhibitory nucleic acid segment to be introduced generally will be substantially identical to at least a portion of the target nematode-induced gene or genes to be repressed. The sequence, however, need not be perfectly identical to inhibit expression. The vectors for use in the present invention can be designed such that the inhibitory effect applies to one or more genes within a family of genes exhibiting homology or substantial homology to the target gene. Similarly, segments from nematode-induced genes from tomato can be used to inhibit expression of homologous genes in different plant species, e.g., using sense or antisense suppression techniques described herein either directly or as a means to obtain the corresponding sequences to be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

B. Plant Transformation

The various DNA constructs described above may be introduced into the genome of the desired plant by a variety of conventional techniques. For example, the DNA construct may be introduced directly into the genomic DNA of the plant cell using polyethylene glycol precipitation (Paszkowski et at. *Embo J.* 3:2717–2722 (1984)) electroporation and microinjection of plant cell protoplasts (Fromm et at. *Proc. Natl. Acad. Sci. USA* 82:5824 (1985)), or the DNA constructs can be introduced into plant tissue using ballistic methods, such as DNA particle bombardment (Klein et al. *Nature* 327:70–73 (1987)). Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. For a review of gene transfer methods for plant and cell cultures see, Potrykus *CIBA Found. Symp.* 154:198 (1990).

*Agrobacterium tumefaciens*-meditated transformation techniques are the most commonly used techniques for transferring genes into plants. These techniques are well described in the scientific literature. See, for example Horsch et al. *Science* 233:496–498 (1984), Fraley et al. *Proc. Natl. Acad. Sci. USA* 80:4803 (1983), and Hooykaas *Plant Mol. Biol.* 13:327–336 (1989).

All species which are a natural plant host for Agrobacterium are transformable in vitro. Most dicotyledonous species can be transformed by Agrobacterium. Monocotyledonous plants, and in particular, cereals, are not natural hosts to Agrobacterium. There is growing evidence now that certain monocots can be transformed by Agrobacterium. Using novel experimental approaches cereal species such as rye (de la Pena et al., *Nature* 325:274–276, 1987), corn (Rhodes et al., *Science* 240:204–207, 1988), and rice (Shimamoto et al., *Nature* 338:274–276, 1989) may now be transformed.

After transformation, transformed plant cells or plants comprising the introduced DNA must be identified. A selectable marker, such as those discussed above is typically used. Transformed plant cells can be selected by growing the cells on growth medium containing the appropriate antibiotic. The presence of opines can also be used if the plants are transformed with Agrobacterium.

After selecting the transformed cells, one can confirm expression of the desired transgenic structural gene or inhibitory RNA. Simple detection of mRNA encoded by the inserted DNA can be achieved by well known methods in the art, such as Northern blot hybridization. The inserted sequence can be identified using the polymerase chain reaction (PCR) and Southern blot hybridization, as well. See, e.g., Sambrook, supra.

Transformed plant cells (e.g., protoplasts) which are derived by any of the above transformation techniques can be cultured to regenerate a whole plant which possesses the transformed genotype and thus the desired nematode resistant phenotype. Such regeneration techniques rely on manipulation of certain phytohormones in a tissue culture growth medium. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The invention has use in producing nematode resistant cultivars of any plant susceptible to infection by these pathogens. The invention thus has use over a broad range of plants, including species from the genera Trifolium, Medicago, Phaseolus, Pisum, Vigna, Glycine, Citrus, Linum, Geranium, Manihot, Daucus, Arabidopsis, Brassica, Raphanus, Capsicum, Datura, Hyoscya mus, Lycopersicon, Nicotiana, Solanum, Petunia, Digitalis, Cichorium, Helianthus, Chrysanthemum, Vitus, Lactuca, Asparagus, Cucumis, Cucurbita, Malus, Pyrus, Prunus, Rosa, Fragaria, Tarro, Ananas, Musa, Cacoa, Beta, Coffea, Gossypium, THea, Dioscorea, Arachis, Citrullus, Juglans, Olea, Cannabis, Triticum, Hordeum, Avena, Festuca, Sorghum, Oryza, Secale, and Zea.

The following examples illustrate, but do not limit, the invention.

EXAMPLE 1

This example describes the construction of a cDNA bank representing genes either uniquely expressed in giant cells (compared to uninfected root cells) or with elevated expression levels. The methods used here combine PCR amplification of cDNA with the efficient and sensitive phagemid subtraction methods to produce a subtracted cDNA bank from a small number of individual tomato giant cells (see, Bird and van der Knaap *Phytopathology* 84:299–303 (1994)). A flow chart outlining the strategy used to construct the library is shown in FIG. 1.

MATERIALS AND METHODS

Culture maintenance. Giant cells and normal root tissue were isolated from in vitro cultured tomato (*Lycoperisicon esculentum* cv 'Rutgers Large Red') plants. Seeds were surface sterilized by vacuum infusion of 0.5% sodium hypochlorite and germinated in parafilm-sealed, petri plates on 2% GelRite containing vitamin supplemented Gamborg's B5 medium. Cultures were maintained in the dark at 26° C. When tertiary root branches were evident (approximately 2 weeks), each dish was inoculated with 200 root-knot nematode (*Meloidogyne incognita*) eggs, surface sterilized by incubation for 10 min in 0.1% streptomycin, 0.0 1% $HgCl_2$. Nematode stocks were maintained on greenhouse grown tomato (cv 'Tropic') plants, and eggs isolated by hypochlorite extraction (McClure et al. *J. Nematol.* 5:230 (1973)).

Root galls containing young adult female nematodes were excised from the etiolated plant-nematode cultures at 1 to 2 months post infection. Gall tissue surrounding the giant cell was dissected away and the exposed, intact nematode removed. Giant cells were resected and snap frozen at −72° C.

RNA isolation. RNA was isolated by a modification of the method of Chomczynski and Sacchi *Anal. Biochem.* 162:156–159 (1987). Approximately 50 mg of giant cells were ground under liquid nitrogen in a micro-homogenizer (Biomedix, Middlesex, UK) and resuspended in 200 µl E-buffer (4M guanidinium isothiocyanate, 25 mM sodium phosphate buffer, pH 7.4, 1% sarkosyl, 1 mM β-mercaptoethanol) at 40° C. The suspension was incubated at 40° C., 20 min, with occasional vortexing. Sodium acetate pH 4 was added to 50 mM followed by an equal volume of water saturated phenol, and the sample placed on ice for 10 min. One-tenth volume of chloroform was added and the aqueous phase recovered following centrifugation at 12,000 g for 10 min at 4° C. The organic phase was back-extracted with 100 µl E-buffer containing 50 mM Na-acetate pH 4 and the aqueous phases pooled. RNA was recovered by ethanol precipitation, dried in vacuo and dissolved in water.

Normal root RNA was extracted from uninfected tissue cultured seedlings grown in parallel and harvested at the same times as giant cells. Freshly harvested tissue was frozen in liquid nitrogen and ground in a mortar and pestle. E-buffer was added at two ml per gram fresh weight of tissue.

cDNA synthesis. Poly-A (+) RNA was captured from giant cell total RNA on oligo-dT$_{25}$ coupled paramagnetic beads (Dynal Inc., Great Neck, N.Y.) according to the manufacturers instructions. Bead-bound RNA was washed twice with 2.5 times the original bead suspension volume of first strand cDNA synthesis buffer (50 mM Tris HCl pH 8.0, 50 mM KCl, 10 mM MgCl$_2$) and cDNA was synthesized on the bead to produce a solid phase primary cDNA pool. First and second strand synthesis and end repair reactions were performed using the Riboclone cDNA synthesis system (Promega, Madison, Wis.) according to manufacturers suggestions. Beads were kept in suspension during the synthesis reactions by shaking at 350 rpm.

Oligonucleotides P35 (GTAAGCGGCCGCAGCGT-CAGTAACTC, Seq. I.D. No. 110) and P36 (TACT-GACGCTGCGGCCGCTTAC, Seq. I.D. No. 111) were annealed using standard conditions (Wu et al. *Meth. Enzymol.* 152:343–349 (1987)). This formed a double stranded adapter molecule, blunt at one end and with a non-complementary, four-base overhang at the opposite end, with an internal NotI site. P36 was end-labeled prior to annealing using polynucleotide kinase. Annealed adapter was ligated onto the free end of the bead-bound dscDNA at 15° C. for 16 h with shaking at 350 rpm. Unligated adapter was removed from the cDNA by washing with sterile water until free counts were no longer detected in the wash.

Second strand cDNA was eluted from bead-bound first strand by heating to 94° C. for three minutes. The beads were then snap chilled on ice and the aqueous phase removed from the beads. cDNA yield was estimated by liquid scintillation counting of an aliquot of the eluate. An additional batch of second strand cDNA was synthesized on the beads by primer extension with P36. Following elution, this material was pooled with the previously synthesized second strand cDNA. Pooled cDNA was converted to double stranded form by extension from the poly-A tract at the 3'-end with P39 primer [ACTCTTGGGCCGAGTTG-GCC(T)$_{15}$](Seq. I.D. No. 112). The dscDNA was purified from excess P39 by spin column chromatography over Sephadex G-50 equilibrated with 200 mM NaCl.

PCR amplification. One fourth of the cDNA was amplified by 15 cycles of PCR (94° C., 2 min; 58° C., 1 min; 72° C., 5 min) using primers P40 [ACTCTTGGGCCGAGTTG-GCC(T)$_4$](Seq. I.D. No. 113) and P36. Amplification products were fractionated on 1% LMP agarose and size ranges of DNA (400–700 bp, 700 bp—1.3 kb, 1.3 kb–5 kb) resected and eluted by Gelase digestion (Epicentre Technologies, Madison, Wis.). One-fifth of each size class was re-amplified by 10 cycles of PCR, using the same conditions as the original amplification. Each reaction was diluted five fold onto fresh reaction mix, and amplified a further 5 cycles. The 400–700 bp, 700 bp 1.3 kb fractions faithfully re-amplified, and were pooled.

cDNA cloning. Single stranded amplification products were removed by mung bean nuclease digestion, and the cDNA was cut with NotI and SfiI. Fifty ng of restricted cDNA insert was ligated into 300 ng of dephosphorylated, NotI-SfiI digested pGem 11 zf(+) vector (Promega, Madison, Wis.). The ligation reaction was phenol extracted, ethanol precipitated, resuspended in 4 µl water, and electroporated at 200Ω, 25 µF, 18.8 kV/cm into 200 µl of electrocompetent *E. coli* DH12s cells (BRL, Gaithersburg, Md.). Cells were incubated for 40 minutes in 100 ml SOC medium at 37° C. with shaking (350 rpm) and an aliquot was removed to determine the number of primary transformants. Ampicillin was added to 50 µg per ml and the culture grown to an A$_{600}$ of 0.1. Two milliliters were removed, grown overnight at 37° C. and stored as a glycerol stock. M13K07 phage were added to the main culture at an moi of 10, and the culture grown for a further 2 h. Phage infected cells were selected by addition of kanamycin to 70 µg/ml, and the culture incubated with vigorous shaking at 37° C. for 15 h.

Recombinant M13 virions were harvested by polyethylene glycol precipitation, and ssDNA prepared and resuspended in 200 µl water. The sample was digested with HindIII and ssDNA purified by fractionation on LMP agarose.

Driver preparation. A solid phase cDNA pool was prepared from 75 µg of uninfected-root total RNA and 10 ng of the resultant double stranded cDNA subjected to 15 cycles of PCR, exactly as described for the giant cell library, except the dTTP concentration was reduced to 75 µM and biotin-16-dUTP (Boehringer Mannheim, Indianapolis, Ind.) added to 25 µM (Lebeau et al. *Nuc. Acids Res.* 19:4778 (1991)). The reaction was diluted five fold and PCR amplification continued for 5 cycles. The final yield of biotinylated cDNA was ~5 µg.

Subtraction and transformation. Biotinylated root cDNA (4 µg) was co-precipitated with 2 µg M13 DNA with giant cell cDNA inserts, giving a ten fold molar excess of driver to insert. The DNA was resuspended in 20 µl water, and 0.5 µg oligo-dT$_{15}$ added. One microliter of 2× hybridization solution (400 mM NaCl, 100 mM Tris HCl pH 7.5, 4 mM EDTA) was added, and the mixture dried in vacuo to 2 µl. The solution was covered with a drop of mineral oil, heated to 94° C. 5 min, and incubated 65° C. for 25 h.

The annealing reaction was diluted to 50 µl with 0.5×SSC and then incubated at room temp for 30 min with 600 µl streptavidin coated paramagnetic beads (Promega, Madison Wis.), previously equilibrated to 0.5×SSC. Beads were separated from the solution on a magnetic stand, and the binding step repeated. Oligo dT$_{15}$ was removed from unbound ssDNA by fractionation on Sephadex G-50/200 mM and salts removed by fractionation on water equilibrated Sephadex G-50. ssDNA was transformed to double stranded form by Klenow extension from P46 primer [GGCCAAGTTG-GCC(T)$_5$](Seq. I.D. No. 114) de-salted on water saturated Sephadex G-50, dried to 3 µl in vacuo and electroporated into *E. coli* DH12s cells. Cells were recovered for one hour in SOC medium and plated with an X-gal/IPTG screen. Insert containing colonies were picked into individual wells of 96 place microtiter plates and glycerol stocks prepared.

Library analysis. Glycerol stocks were replica-stamped onto nitrocellulose membranes and were probed with nick-translated genomic tomato and nematode DNA and cDNA inserts using standard conditions (Wahl et al. *Proc. Natl. Acad. Sci. USA* 76:3683–3687 (1979)).

ssDNA was prepared from recombinants by rescue with the helper phage M13K07 and subjected to sequencing using the dideoxy chain-termination method (Sanger et al., *Proc. Natl. Acad. Sci. USA* 74:5463 (1977)). Hybridization probes for Southern and RNA dot blot analyses were prepared by primer extension of single stranded templates with universal sequencing primer. Tomato and nematode genomic DNA was prepared by grinding in liquid nitrogen followed by proteinase K digestion and phenol/chloroform extraction.

RESULTS cDNA synthesis. Fifty one milligrams of essentially pure giant cells were accumulated by dissection. Based on comparative ethidium bromide fluorescence, the yield of total RNA from this sample was estimated to be 11 µg. This represents a yield per gram fresh weight of tissue of approximately 4 fold higher than we obtain from cultured whole roots, and possibly is a reflection of increased transcriptional activity in giant cells.

Performing the cDNA synthesis on paramagnetic beads provided a number of advantages over liquid synthesis, including the ability to readily recover poly-A(+) RNA and cDNA into essentially zero volume. Because the bead effectively blocked one end, addition of a NotI adapter after cDNA synthesis was restricted to the 5'-end (with respect to the message). Additionally, the use of solid phase cDNA synthesis provided a reusable pool of first strand cDNA.

Based on incorporation of $^{32}$P-labeled P36 (half of the adapter), conversion of poly-A(+) RNA into eluted second strand cDNA was 24%. Subsequent re-synthesis of second strand cDNA corresponded to a 15% conversion of poly-A(+) RNA. It is likely that this reduced efficiency resulted from inefficient priming. Conversion of pooled, eluted second strand cDNA to double stranded form by priming with an oligo-dT-anchored, SfiI primer (P39) yielded 43 ng of double stranded cDNA. Analysis of an aliquot by electrophoresis on alkaline agarose revealed an average size of 800 bases for this cDNA pool, with a portion extending larger.

Pilot experiments indicated that, under our conditions, the rate of amplification began to diminish between 10 and 15 rounds of PCR while, in pari passu, the amount of single stranded product increased. Consequently, the giant cell cDNA was subjected to only 15 cycles of PCR amplification prior to size fractionation. The size classes were re-amplified and single stranded strand amplification products removed by mung bean nuclease digestion prior to cloning. Comparison of cDNA before and after nuclease treatment indicated that up to two thirds of the amplified cDNA, primarily the larger material, consisted of single strand product. The average size of the final cDNA population was about 300 bp, with a range of 200 to 500 bp. Preferential extension of smaller cDNAs over larger ones as PCR progresses has been observed previously (Belyavsky et al. *Nuc. Acids Res.* 17:2919–2932 (1989)).

Cloning. To maximize the efficiency of the cloning step, and also to eliminated the possibility of cloning uninfected-root driver cDNA, amplified giant cell cDNA was ligated into a phagemid vector. A test plating of the library at this stage indicated that it contained $1.4 \times 10^6$ transformants. Following conversion to single stranded form by rescue with M13K07, the cloned giant cell cDNAs were annealed with normal-root cDNA driver to a Cot value of 500. Using a k value for a typical mammalian cell (15,000 unique transcripts), the fraction of cDNAs common both to uninfected roots and giant cells that have annealed at Cot 500 is 96.5%.

After the annealed cDNA had been removed, the single stranded recombinants were converted to double stranded form. Transformation by electroporation of double stranded plasmid DNA has been shown to be several hundred fold more efficient than single stranded plasmid DNA. We utilized a primer which spans the SfiI cloning site and the poly-A tail of the insert. This primer is not complementary to either insert-minus or to incorrectly oriented insert-containing clones. Production of double stranded plasmid DNA prior to transformation with this primer allowed for more efficient cloning of genuine subtracted clones over insert-minus or aberrant clones which may have escaped the subtraction procedure.

Following transformation, 287 insert-containing clones, as determined by blue/white colony screening, were recovered. This corresponded to an overall enrichment of 4,860 fold of giant cell sequences over normal root sequences present in the cDNA library. This figure is substantially higher than is typically obtained by subtraction.

Library analysis. A variety of criteria were used to assess the overall quality of the subtracted library. Insert size was determined by restriction analysis. Inserts resected from ten randomly selected clones ranged in size from 200 to 500 bp in length. Seven of these probes were also hybridized back to the entire library. One clone detected two recombinants; the remaining six probes detected only the clones from which they were constructed. This result suggests that the complexity of the subtracted library might be high.

The total number of highly repeated genomic sequences represented in the library was determined by hybridization of replica filters with nick translated tomato total genomic DNA. Forty two of the 287 clones gave a high signal. Four of these clones were sequenced; three were derived from 25S rRNA and one from 16S rRNA. To further confirm that clones not detected in this assay were indeed derived from low copy number genes, genomic Southerns were performed using 36 randomly selected clones as probes. Hybridization banding patterns identified one apparently multicopy gene. However, most appear to be low copy or unique genes. These results also confirm that the clones are of plant origin. To determine the number of contaminating nematode sequences in the library, the replica filters were probed with nick-translated *Meloidogyne incognita* total genomic DNA. One colony gave a signal detectable above background. A second clone encoding a nematode transcript was subsequently identified by genomic blotting.

Dot blots of RNA samples isolated from tomato tissues (galls and whole mature roots from tissue culture, mature leaf from green-house grown plants, and cotyledons, hypocotyls and roots from one-week-old seedlings) were hybridized with probes synthesized from randomly selected giant cell cDNA clones. In these experiments, 5 µg of total RNA isolated from various tomato tissues was blotted onto nitrocellulose and hybridized with primer extended $^{32}$P labeled antisense probes. Hybridization probes were prepared by primer extension of half of the annealed sequencing DNA template in the presence of α-[$^{32}$P]-dCTP. The specific activity of these probes typically was $2 \times 10^9$ dpm/µg. Filters were probed using standard conditions (Wahl et al. *Proc. Natl. Acad. Sci. USA* 76:3683–3687 (1979)). The presence of equal amounts of target RNA in each dot was confirmed by probing with ribosomal sequences. The exposure times varied significantly between the different filters. This variation is indicative of differences in transcript abundance because the specific activities and amount of probe used in each experiment was essentially the same.

Results from these experiments are summarized in Table 1 (clones which were not sequenced and which gave no blot results have been omitted). Sixteen probes failed to produce a detectable hybridization signal to any of the RNA samples, suggesting that these cDNAs represent low abundance messages. The remaining cDNA clones hybridized to various subsets of the RNA samples.

TABLE 1

DNA sequence and RNA dot blot analysis of giant cell cDNA clones

| DB # | SEQ. ID. No. | Identity[2] | Tissue source of RNA[1] | | | | | |
|---|---|---|---|---|---|---|---|---|
| | | | G | D | L | H | A | R |
| 101 | SEQ. ID. No. 1 | Pioneer | | | | | | |
| 102 | SEQ. ID. No. 2 | Pioneer | | | | | | |
| 103 | SEQ. ID. No. 3 | 16 kD $E_2$ enzyme | − | − | − | + | + | − |
| 107 | SEQ. ID. No. 4 | Peroxidase | − | − | − | − | − | − |
| 108 | SEQ. ID. No. 5 | Pioneer | − | − | − | − | − | − |
| 110 | SEQ. ID. No. 6 | Pioneer | | | | | | |
| 111 | SEQ. ID. No. 7 | Pioneer | | | | | | |
| 112 | SEQ. ID. No. 8 | Pioneer | | | | | | |
| 113 | SEQ. ID. No. 9 | Pioneer | − | − | − | − | − | + |
| 114 | SEQ. ID. No. 10 | Pioneer | + | − | + | + | + | − |
| 115 | SEQ. ID. No. 11 | Pioneer | + | − | + | + | + | − |
| 117 | SEQ. ID. No. 12 | RNA pol ll Heptamer repeat | | | | | | |
| 118 | SEQ. ID. No. 13 | Pioneer | − | − | − | − | − | − |
| 119 | SEQ. ID. No. 14 | Pioneer | − | − | − | − | − | − |
| 122 | SEQ. ID. No. 15 | Extenin-like pioneer | − | − | − | − | − | − |
| 124 | SEQ. ID. No. 16 | Pioneer | + | ? | − | − | − | − |
| 131 | SEQ. ID. No. 17 | Receptor kinase homologue | + | − | − | − | − | − |
| 132 | SEQ. ID. No. 18 | Anti-integral membrane protein | + | − | − | + | − | − |
| 133 | SEQ. ID. No. 19 | Zea repetitive element/cyclophylin 3' | + | − | + | + | + | + |
| 134 | SEQ. ID. No. 20 | Pioneer | − | − | − | + | − | − |
| 136 | SEQ. ID. No. 21 | 16 kD $E_2$ enzyme | | | | | | |
| 137 | SEQ. ID. No. 22 | Pioneer | − | − | − | + | + | − |
| 139 | SEQ. ID. No. 23 | Pioneer | + | − | + | − | − | + |
| 140 | SEQ. ID. No. 24 | Pioneer | + | − | + | − | − | + |
| 141 | SEQ. ID. No. 25 | Pioneer | + | − | − | + | + | − |
| 142 | SEQ. ID. No. 26 | anti-Ef-3 | − | − | − | − | + | − |
| 144 | SEQ. ID. No. 27 | Ribosomal protein L38 | | | | | | |
| 146 | SEQ. ID. No. 28 | Pioneer | | | | | | |
| 147 | SEQ. ID. No. 29 | Pioneer | | | | | | |
| 148 | SEQ. ID. No. 30 | Pioneer | | | | | | |
| 149 | SEQ. ID. No. 31 | Pioneer | | | | | | |
| 151 | SEQ. ID. No. 32 | Pioneer | | | | | | |
| 152 | SEQ. ID. No. 33 | Pioneer | | | | | | |
| 153 | SEQ. ID. No. 34 | Anti-ripening associated membrane prot | | | | | | |
| 154 | SEQ. ID. No. 35 | Pioneer | | | | | | |
| 155 | SEQ. ID. No. 36 | Pioneer | | | | | | |
| 156 | SEQ. ID. No. 37 | Pioneer | | | | | | |
| 157 | SEQ. ID. No. 38 | Pioneer | | | | | | |
| 161 | SEQ. ID. No. 39 | Pioneer | − | − | − | − | − | − |
| 163 | SEQ. ID. No. 40 | 16 kD $E_2$ enzyme | − | − | − | + | + | − |
| 164 | SEQ. ID. No. 41 | Pioneer | − | − | − | − | − | + |
| 165 | SEQ. ID. No. 42 | Pioneer | − | − | + | − | − | − |
| 166 | SEQ. ID. No. 43 | Pioneer | − | − | + | − | + | − |
| 168 | SEQ. ID. No. 44 | Mucin | | | | | | |
| 169 | SEQ. ID. No. 45 | Novel 16 kD $E_2$ enzyme | | | | | | |
| 172 | SEQ. ID. No. 46 | L38 ribosomal protein | | | | | | |
| 173 | SEQ. ID. No. 47 | Pioneer | + | + | + | − | − | + |
| 175 | SEQ. ID. No. 48 | Pioneer | | | | | | |
| 176 | SEQ. ID. No. 49 | Pioneer | | | | | | |
| 177 | SEQ. ID. No. 50 | Proline-rich wall protein | | | | | | |
| 178 | SEQ. ID. No. 51 | Pioneer | | | | | | |
| 179 | SEQ. ID. No. 52 | Pioneer | | | | | | |
| 181 | SEQ. ID. No. 53 | Transmembrane turgor-responsive prot | | | | | | |
| 182 | SEQ. ID. No. 54 | Pioneer | | | | | | |
| 183 | SEQ. ID. No. 55 | Pioneer | | | | | | |
| 187 | SEQ. ID. No. 56 | Pioneer | | | | | | |
| 197 | SEQ. ID. No. 57 | Pioneer | − | − | − | − | − | − |
| 198 | SEQ. ID. No. 58 | Pioneer | | | | | | |
| 199 | SEQ. ID. No. 59 | anti-Ala tRNA synthase | − | − | − | − | + | − |

TABLE 1-continued

DNA sequence and RNA dot blot analysis of giant cell cDNA clones

| DB # | SEQ. ID. No. | Identity[2] | G | D | L | H | A | R |
|---|---|---|---|---|---|---|---|---|
| 201 | SEQ. ID. No. 60 | Pioneer | | | | | | |
| 203 | SEQ. ID. No. 61 | Pioneer | − | − | − | − | − | − |
| 205 | SEQ. ID. No. 62 | Pioneer | | | | | | |
| 207 | SEQ. ID. No. 63 | Pioneer | − | − | − | − | − | − |
| 208 | SEQ. ID. No. 64 | Pioneer | − | − | − | − | − | − |
| 209 | SEQ. ID. No. 65 | Pioneer | | | | | | |
| 210 | SEQ. ID. No. 66 | Pioneer | − | − | − | − | + | − |
| 212 | SEQ. ID. No. 67 | Pioneer | − | − | − | − | + | − |
| 214 | SEQ. ID. No. 68 | Pioneer | − | − | − | − | − | − |
| 215 | SEQ. ID. No. 69 | Zn-finger domain | − | − | − | − | + | − |
| 216 | SEQ. ID. No. 70 | Pioneer | − | − | − | − | − | − |
| 217 | SEQ. ID. No. 71 | Laminin B receptor | + | − | + | − | − | + |
| 218 | SEQ. ID. No. 72 | Pioneer | | | | | | |
| 220 | SEQ. ID. No. 73 | anti-PEP-carboxylase | − | − | − | − | − | − |
| 221 | SEQ. ID. No. 74 | Pioneer | − | − | + | − | − | − |
| 222 | SEQ. ID. No. 75 | Pioneer | − | − | − | − | − | |
| 223 | SEQ. ID. No. 76 | Pioneer | − | − | − | − | − | − |
| 224 | SEQ. ID. No. 77 | Pioneer | − | − | − | − | − | − |
| 226 | SEQ. ID. No. 78 | Proton ATPase | − | − | − | + | − | − |
| 227 | SEQ. ID. No. 79 | Pioneer | | | | | | |
| 228 | SEQ. ID. No. 80 | anti-L11 ribosomal protein | | | | | | |
| 230 | SEQ. ID. No. 81 | Pioneer | | | | | | |
| 231 | SEQ. ID. No. 82 | Pioneer | | | | | | |
| 232 | SEQ. ID. No. 83 | Pioneer | | | | | | |
| 233 | SEQ. ID. No. 84 | Pioneer | | | | | | |
| 234 | SEQ. ID. No. 85 | Lysozyme-domain | + | ? | − | + | + | + |
| 236 | SEQ. ID. No. 86 | Pioneer | | | | | | |
| 239 | SEQ. ID. No. 87 | eF Ile 5'UTR | − | − | − | + | + | − |
| 240 | SEQ. ID. No. 88 | Pioneer | − | − | − | + | + | − |
| 241 | SEQ. ID. No. 89 | Pioneer | | | | | | |
| 244 | SEQ. ID. No. 90 | Pioneer | − | − | + | − | + | − |
| 246 | SEQ. ID. No. 91 | Pioneer | | | | | | |
| 247 | SEQ. ID. No. 92 | Pioneer | | | | | | |
| 249 | SEQ. ID. No. 93 | Tob RB7-5A homologue | | | | | | |
| 250 | SEQ. ID. No. 94 | Pioneer | | | | | | |
| 252 | SEQ. ID. No. 95 | Pioneer | + | − | − | + | + | + |
| 255 | SEQ. ID. No. 96 | Pioneer | | | | | | |
| 256 | SEQ. ID. No. 97 | Pioneer | | | | | | |
| 263 | SEQ. ID. No. 98 | Pioneer | − | − | − | + | + | + |
| 264 | SEQ. ID. No. 99 | Pioneer | | | | | | |
| 265 | SEQ. ID. no. 100 | anti-Tnt1-94 tranposon | − | − | − | + | + | + |
| 266 | SEQ. ID. No. 101 | Pioneer | | | | | | |
| 275 | SEQ. ID. No. 102 | Pioneer | − | − | − | + | + | − |
| 277 | SEQ. ID. No. 103 | Pioneer | | | | | | |
| 279 | SEQ. ID. No. 104 | Pioneer | − | − | − | − | − | + |
| 280 | SEQ. ID. No. 105 | Myb DNA-binding site | − | − | − | + | + | − |
| 288 | SEQ. ID. No. 106 | Pioneer | | | | | | |
| 289 | SEQ. ID. No. 107 | Pioneer | | | | | | |
| 291 | SEQ. ID. No. 108 | Pioneer | | | | | | |
| L23762 | SEQ. ID. No. 109 | Ubiquitin carrier protein | | | | | | |

[1]RNA samples from the tissues indicated (G: gall; D: RNA isolated from cultured, uninfected roots, and used as driver for the subtractive cloning; L: leaf; H: hypocotyl; A: cotyledons plus apex; R: primary root from young seedlings) were probed with anti-sense probes from the cDNA clones: + indicates a signal was detected, − indicates no signal was detected, no entry indicates that the clone was not tested.
[2]Putative identity of partial cDNA clones based on DNA or deduced amino acid homology with sequences in GenBank or PIR. Clones with no meaningful homology were termed pioneers.

Only one clone (DB#173) produced a signal in the RNA from mature roots. This is important because mature root was the source of the RNA used as driver in construction of the subtractive library, and provides strong evidence that the subtraction was effective. Fifteen of the cDNA clones detected transcripts in seedling root (Table 1), and presumably encode functions associated with young, expanding roots. Three of these appeared to be root-specific.

Despite the fact that only cDNA synthesized from giant cell mRNA was exposed to the vector thereby ensuring that all clones in the bank must encode giant cell transcripts, most probes also failed to detect transcripts in gall RNA. Although this is partly due to giant cells representing only a small fraction of the total mass of the gall (it was not technically feasible to collect the numbers of giant cells required to isolate sufficient RNA for blot analysis), it also suggests that the clones in the bank do not encode abundant transcripts. Ultimately, the (elevated) presence in giant cells of transcripts defined by each clone in the bank can be confirmed using, for instance, in situ hybridization.

Although different clones reveal a range of expression patterns, many detected transcripts in RNA isolated from hypocotyls and/or cotyledon plus apex tissue, generally at levels much higher than in uninfected seedling root. Ten cDNA clones detected a signal in leaf RNA. Overall, these results give a picture of giant cells sharing transcripts with actively dividing and expanding tissues, and also non-root tissues.

DNA sequencing

Partial sequences of each clone listed in Table 1, above, are provided in the Sequence Listing, below. The Sequence Listing also includes the complete sequence of one clone, SEQ. ID. No. 109, which encodes a ubiquitin carrier protein. Reflective of the directional nature of the cloning, each sequence began with a poly-T tract (ranging in length from 4 to 75 residues), corresponding to the poly-A tail of the transcript. Each sequence was read only as far as the first ambiguity, including potential compressions. Thus, although the sequences represent readings from one strand only, we believe the degree of accuracy to be high. The presence of a long oligomeric tail rendered some clones unsequencable. Four independent rRNA clones from the same bank also were determined. The sequences (not shown) corresponded exactly to those published for tomato (Kiss et al. *Nucl. Acids Res.* 17:796 (1989)). This suggests also that the number of PCR-introduced artifacts in the bank is low.

Sequences were compared to others in the public domain DNA and protein databanks using the BlastN and BlastX algorithms (Altschul et al. *J. Mol. Biol.* 215:403–410 (1990)). With some exceptions noted below, only those database matches involving homology with the correct strand and in the correct part of the matching gene (i.e., the 3'-end) were considered, and a score of at least 100 was chosen as indicating a potentially valid homology. Most of the cDNA sequences failed these tests, and are listed as "Pioneers" in Table 1. Four clones were determined to share sequences with genes previously cloned in tomato, all other non-pioneers shared sequences with sequences from other species.

By isolating and characterizing full length cDNA clones, including in situ localization to giant cells the identity of the DB#103 transcript was confirmed as encoding an $E_2$ enzyme, a key component of the protein ubiquitination pathway.

The DB#163 cDNA is identical with the DB#103 sequence, but has an additional 19 residues immediately before the poly-A tail. Because the gene encoding these transcripts, LeUBC10, appears to be unique, the different 3'-ends might arise by differential RNA processing.

Computer translation of the DB#117 cDNA revealed a hypothetical protein with multiple contiguous repeats of a seven amino acid motif, shown aligned in FIG. 2, and terminating with a stop codon 47 bp 5' from the poly-A tail. This motif is strikingly similar to the motif TSPSYSP, a structure diagnostic for the carboxy terminal domain (CTD) of the large subunit of RNA polymerase II. Arabidopsis has 40 copies of this repeat (Dietrich et al. *Plant Mol. Biol.* 15:207–223 (1990)) and *C. elegans* has 42 (Bird and Riddle *Molec. Cell. Biol.* 9:4119–4130 (1989). Although not previously cloned from tomato, it seems likely that DB#117 encodes this gene. Southern blotting (not shown) suggests that the DB#117 region is unique.

BlastX analysis revealed significant homologies between the inferred DB#280 product and different members of the myb gene family (FIG. 3). Homology is highest with the DNA binding domain of the petunia myb Ph3 gene product, although multiple alignment with Mybs from other plants and vertebrates revealed that this homology extends further. As nuclear transcription regulators, members of the Myb family play pivotal roles in the regulation of cellular proliferation. Through interactions with other trans-activators (e.g., members of the Ets family) Myb proteins effect growth control and oncogenesis.

A BlastN search revealed striking homology between the DB#226 sequence and the 3'-end of the pma4-encoded isoform (Moriau et al. *Plant Molec. Biol.* 21:955–963 (1993)) of a plasmalemma $H^+$ATPase from *Nicoaana plumbaginifolia* (FIG. 4). The DB#226-gene appears to be different from those encoding two previously cloned tomato isoforms (Ewing et al. *Plant Physiol.* 94:1847–1881 (1990)). The high degree of homology between the 3' untranslated regions (UTR) of these genes (the tobacco stop codon, and presumably also the DB#226 terminator, is a further 60 residues 5') might indicate a biological role for this part of the sequence.

Other sequences in the giant cell cDNA bank, including a number of the pioneer clones, encode recognizable structural motifs. For example, part of the DB#215 sequence specifies a zinc finger domain. Additional homologies have been observed in the UTRs of some genes. The 3'-UTR of DB#239 contains a $(GCC)_5$ element previously noted in the 5'-UTR of human general transcription factor TFIIE (Sumimoto et al. *Nature* 354:401–404 (1991); sequences such as these may play a role in translational regulation.

Four clones in the cDNA bank (DB#142, DB#199, DB#220, DB#265) have high degrees of homology with sequences in GenBank (Blast scores of 246, 499, 806 and 173 respectively) but to the anti-sense strand. These sequences terminate with a poly-A tail, suggesting that they do not represent artifactuary cloned sequences. Significantly, when used as probes in the dot blot assay, DB#142, DB#199, and DB#265 detected transcripts in plant tissues (Table 1). The DB#265 transcript, which encodes a sequence with anti-sense homology to the tobacco retroviral-like transposon Tnt 1-94 (Grandbastien et al. *Nature* 337:376–380 (1989)), and also the Arabidopsis copia-like element (Voytas and Ausubel *Nature* 336:242–244 (1989)), appears to be particularly abundant in seedling root tissue.

The cDNA clone DB#249 as a query revealed that its inferred product shares homology with that of the RB7-5A gene from tobacco (Yamamoto et al. *Nuc. Acids Res.* 18:7449 (1990)). Significantly, this gene is strongly up-regulated in nematode-induced, tobacco giant cells.

Taken together, these data show the subtracted library contains bona fide cDNA inserts with a low level of contamination by high copy or nematode sequences, as well as a high degree of complexity.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated polynucleotide capable of hybridizing under stringent conditions to a nucleic acid having the sequence of SEQ. ID. No. 17.

* * * * *

SEQUENCE LISTING ( 1 ) GENERAL INFORMATION:

( i i i ) NUMBER OF SEQUENCES: 114

( 2 ) INFORMATION FOR SEQ ID NO:1:

( i ) SEQUENCE CHARACTERISTICS:
        ( A ) LENGTH: 210 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..210
        ( D ) OTHER INFORMATION: /standard_name="DB#101"

( x i ) SEQUENCE DESCRIPTION: SEQ ID NO:1:

```
ACACGATCAC ATACCAGAGG GCAGACAACC AAGCTGAGAG GTCAAGTGGG TCTGGGAGTT      60

CAATTTCCAA GTCTATGAAA ACCAGTTCTT CAACAAGTTC CGGTGCTGAT CCTTCATTGG     120

TTCAAGCATC ATTGTTAGAT AGTATATTGA GGGAGAACCT CTTGTGATCT GGAGAAAGTA     180

ACCTATTACA GTATTTTGTA CCTCTTACGT                                      210
```

( 2 ) INFORMATION FOR SEQ ID NO:2:

( i ) SEQUENCE CHARACTERISTICS:
        ( A ) LENGTH: 211 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..211
        ( D ) OTHER INFORMATION: /standard_name="DB#102"

( x i ) SEQUENCE DESCRIPTION: SEQ ID NO:2:

```
CATAAACCTG TTTTTCTCTT TCCCCCTTAT GATGAATCCA GTCTATGAAG TAATGGAAAG      60

GAGATTCTGG GAAGGCAGGT ACTGTGTGTG GTTGAGATGG CTTGTGGTTT TAGCAGTGAC     120

TTTTGTTGCA TTGGCGGTGC CCAATTGTTG CTGATTCTTT CACTTGTTGG GAGCAGTGTG     180

TGCATTGTTT TGGGATTTGT GTTGCCTTCT T                                    211
```

( 2 ) INFORMATION FOR SEQ ID NO:3:

( i ) SEQUENCE CHARACTERISTICS:
        ( A ) LENGTH: 257 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..257
        ( D ) OTHER INFORMATION: /standard_name="DB#103"

( x i ) SEQUENCE DESCRIPTION: SEQ ID NO:3:

| | | | | | |
|---|---|---|---|---|---|
| AACTGGCAAA | CAAAGTAGAA | TTACATTGCA | GTTTCTCCCT | TACTAGTCAT | CAAATAAATA | 60
| TTCACAAATT | GAAAACAGCT | GTTCCCTTAA | CAACCCTCAT | GAAGGGAGAT | TAAGAAGTAA | 120
| CTAAGTTCTT | TCACGGAATT | TATTCATTCA | CCCCAAGCAC | ATAAGACATT | GCTGTTACAA | 180
| AGTCCCAGAC | ATGCCTGGAG | ACATTTGCG | CATCATCCA | TTGCATATTT | CTGAGTCTAG | 240
| CTACGAGCAG | TGGTTTC | | | | | 257

( 2 ) INFORMATION FOR SEQ ID NO:4:

( i ) SEQUENCE CHARACTERISTICS:
        ( A ) LENGTH: 249 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..249
        ( D ) OTHER INFORMATION: /standard_name="DB#107"

( x i ) SEQUENCE DESCRIPTION: SEQ ID NO:4:

| | | | | | |
|---|---|---|---|---|---|
| AGGGTCAAAT | TTGGAATTGC | AGTTTGCTCA | CTTGGCCCTC | CTGCTGATCC | ATCTAGCAAC | 60
| ACTGAACCAT | CACACCCCTG | AACAAAGCAA | TCGTGGAAAT | GAAGACGAAG | TAAGCCAGCA | 120
| GCTTGGCCAA | CATCATCCTT | GATTTGTTTT | TGAAGCCTGT | TTCTAATAAT | GGATTCAAGT | 180
| TGAGGACAAC | TAGATTGATA | AATGACCATG | AGACCTTAGT | TAGCAGCCTT | GAGCTTCCGA | 240
| TCAAGATTT | | | | | | 249

( 2 ) INFORMATION FOR SEQ ID NO:5:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..132
        ( D ) OTHER INFORMATION: /standard_name="DB#108"

( x i ) SEQUENCE DESCRIPTION: SEQ ID NO:5:

| | | | | | |
|---|---|---|---|---|---|
| GGGATTACTG | AGGTGGTTTT | GGATCTTTCT | TCCGGCCTTT | CGCTATATAC | ACAAGATAGG | 60
| ACAATGATCA | GTAGTTGTTT | GTTGTTGTCC | TTTGTCCTGA | GACTTTGTC | ATGTTAATGG | 120
| GGTTTCCAAT | GC | | | | | 132

( 2 ) INFORMATION FOR SEQ ID NO:6:

( i ) SEQUENCE CHARACTERISTICS:
        ( A ) LENGTH: 207 base pairs
        ( B ) TYPE: nucleic acid
        ( C ) STRANDEDNESS: single (D) TOPOLOGY: linear (ii) MOLECULE TYPE: DNA (genomic)

(vi) ORIGINAL SOURCE:
    (A) ORGANISM: Lycopersicon esculentum cv 'Rutgers Large Red'

(ix) FEATURE:
    (A) NAME/KEY: misc_feature
    (B) LOCATION: 1..207
    (D) OTHER INFORMATION: /standard_name="DB#110"

(xi) SEQUENCE DESCRIPTION: SEQ ID NO:6:

| | | | | | |
|---|---|---|---|---|---|
| AGCAGTCCCT | TTGGGTGTCA | CAATTTTCTC | AGCACTTGAA | CTCAAGCCAT | TAGGATCAAT | 60 |
| GTTATTCCCT | CTCTTAATAG | CTGGTAGTCT | TGGCGACTTC | ATTTTGTGGT | CGCTGCTTTA | 120 |
| GATCTGTTAC | ATATTAGCGG | CTTTTCTTTT | GTAGCATCTC | AGTTAGAAAG | TACTGGACGT | 180 |
| GCCTTTTCTT | TGCGCACGAT | AAACACG | | | | 207 |

(2) INFORMATION FOR SEQ ID NO:7:

(i) SEQUENCE CHARACTERISTICS:
    (A) LENGTH: 256 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Lycopersicon esculentum cv 'Rutgers Large Red'

(ix) FEATURE:
    (A) NAME/KEY: misc_feature
    (B) LOCATION: 1..256
    (D) OTHER INFORMATION: /standard_name="DB#111"

(xi) SEQUENCE DESCRIPTION: SEQ ID NO:7:

| | | | | | |
|---|---|---|---|---|---|
| AAATTACACC | CATTTTATCA | ACCTTGGAGT | AAATCTTACC | AGCACTAAAC | TGGCTTACAA | 60 |
| TGCCATGGGC | AGTTCGCTCA | ATAACAATTC | ATCTAAAACA | TTTTGAAGG | CACTGTGCTA | 120 |
| ATGTTTCTAA | CACATAAAAT | TGAATCTAAG | GTCCAAAATT | TAGTTTTCAT | TACAGAGGCA | 180 |
| GCCAAGAATG | CAAACAACTA | CCAACCATGC | ATTTGCATGA | CTGTGGATCT | TCAACTTCAT | 240 |
| CTCACAACTA | ACGCAT | | | | | 256 |

(2) INFORMATION FOR SEQ ID NO:8:

(i) SEQUENCE CHARACTERISTICS:
    (A) LENGTH: 179 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Lycopersicon esculentum cv 'Rutgers Large Red'

(ix) FEATURE:
    (A) NAME/KEY: misc_feature
    (B) LOCATION: 1..179
    (D) OTHER INFORMATION: /standard_name="DB#112"

(xi) SEQUENCE DESCRIPTION: SEQ ID NO:8:

| | | | | | |
|---|---|---|---|---|---|
| GGTATGTTGT | ACGCTGCTGT | TGAAGTTGAA | GATCTGAAGA | TGCGTTTGCT | GCTGTTGGAA | 60 |
| GTTAAATCAT | TTGGTCACA | CTGTTGGGTT | GTTCCTGTTA | CATTTGGAAA | CACTCAACTT | 120 |

TTAACTCCTA AACTTGTTGC TGTTGCTTGT CTGAATCTGT CGTGTGCATC ATTAACACA 179

( 2 ) INFORMATION FOR SEQ ID NO:9:

( i ) SEQUENCE CHARACTERISTICS:
        ( A ) LENGTH: 210 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..210
        ( D ) OTHER INFORMATION: /standard_name="DB#113"

( x i ) SEQUENCE DESCRIPTION: SEQ ID NO:9:

CTTAAAAGCT AGTCTTTCTT AGGTTCACAT AGCAGTTACT TCCAAAAGTT AAAACATAAA 60

TCAAAATTAT CCCATTACAT CATTTAACTG AAGGGAGATG CAAATCAAAA AGCTCTAATG 120

CCATATGTCT TCTACCAGCA CCAAATGTAG AGGTCCTCGT AGAAACTCGT ATTCAAGATT 180

TTTAACGGTA CTTGATGAAG CCAATTCCTT 210

( 2 ) INFORMATION FOR SEQ ID NO:10:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..110
        ( D ) OTHER INFORMATION: /standard_name="DB#114"

( x i ) SEQUENCE DESCRIPTION: SEQ ID NO:10:

AGGAGGTTTA TCTGATACAG TTGACTTGAA ATATGGCATA TTGGGTCTTA AGCCAACATC 60

TGCTTCAGTC ATCTTATCCA AAACTGACTT GACAAGTTCA ACATTTTCCG 110

( 2 ) INFORMATION FOR SEQ ID NO:11:

( i ) SEQUENCE CHARACTERISTICS:
        ( A ) LENGTH: 223 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..223
        ( D ) OTHER INFORMATION: /standard_name="DB#115"

( x i ) SEQUENCE DESCRIPTION: SEQ ID NO:11:

```
GAGCTCAACT  AGTCGAGCTA  GTAAGAAGAG  AGATTATAAT  TGTAAAATCA  CTCACCAATA     60

CCTGCATTAT  ACACACCAAA  TGTAAGGCAA  ATATAAGAAT  TCACTTATTT  AGCTTCTTCT    120

GGATCTACTT  TGATAGAAAG  CGCAGTGGTA  CATGGTGGAT  GAGCAAGACG  AACAATACTT    180

CAAAGAAGAC  CATCATGAAA  GTTGTTGACA  TGCTTTAATC  AGT                       223
```

( 2 ) INFORMATION FOR SEQ ID NO:12:

( i ) SEQUENCE CHARACTERISTICS:
        ( A ) LENGTH: 279 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..279
        ( D ) OTHER INFORMATION: /standard_name="DB#117"

( x i ) SEQUENCE DESCRIPTION: SEQ ID NO:12:

```
GTAACCACCG  TCGTATTTTC  CGCCGATACC  CATCGTCGTA  GCTGGGCTTA  TAACCTGTCG     60

TAGCTTGGCT  TGTAATTGTC  ATAGCTAGGC  TTGTAACTGT  CGTAGCTTGG  CTTGTAATTG    120

TCATAGCTAG  GCTTGTAACT  GTCGTAGCTT  GGCTTGTATC  CGCTGTCGTA  GCTAGGCTTT    180

TTGTAACCAT  TGTCGTAGCT  GGGCTTGTAT  CCGCTGTCGT  AGCTGGGCTT  TTTGTAACTA    240

TTGTCATAGC  TGGGCTTGTA  GCTGTCTGAG  CTGGGCTTT                             279
```

( 2 ) INFORMATION FOR SEQ ID NO:13:

( i ) SEQUENCE CHARACTERISTICS:
        ( A ) LENGTH: 267 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..267
        ( C ) OTHER INFORMATION: /standard_name="DB#118"

( x i ) SEQUENCE DESCRIPTION: SEQ ID NO:13:

```
AGAGTGAAAT  CTTCAAAATA  GCAGTAAAAT  TGGTACCTTC  ACTATAACTG  GTGTTTCATA     60

TTTTTCTTAG  CTAGAATGCA  GTTGATTTGT  TACAACAAAT  ACTGAGTTAA  TGAGGCCTTG    120

TAGTAGTAAG  TTGGGACCAA  ATTGGATTTC  TCATCATTAG  ATTGTTTGTC  CAGTTACTAC    180

CTTCAGGTAG  ACAAATATAC  TTAGTAAGAG  GAGAAACCAA  TGGAAGAGAA  GGTGATTGTA    240

GCCATGGTTA  GGGCATGTTT  CTTGGCT                                           267
```

( 2 ) INFORMATION FOR SEQ ID NO:14:

( i ) SEQUENCE CHARACTERISTICS:
        ( A ) LENGTH: 199 base pairs
        ( B ) TYPE: nucleic acid
        ( C ) STRANDEDNESS: single (D) TOPOLOGY: linear (ii) MOLECULE TYPE: DNA (genomic)

(vi) ORIGINAL SOURCE:
    (A) ORGANISM: Lycopersicon esculentum cv 'Rutgers Large Red'

(ix) FEATURE:
    (A) NAME/KEY: misc_feature
    (B) LOCATION: 1..199
    (D) OTHER INFORMATION: /standard_name="DB#119"

(xi) SEQUENCE DESCRIPTION: SEQ ID NO:14:

```
ACCTACCACC TCCCACCGGC AATAGGTACA GTCCACCAAG GCTAGGACAG ATGGAAATAA      60
CTACCTAGTG TTTTCTTGTC TCCGCTAGAA ACAAAATTAG CTAGTTTTCA TCTTCAAGAT     120
CCAAACAAAG GCAGTAAGCA ACTAAGCCAC AACTGAACAT ATCTGAGATA TCTCACTATG     180
TCAGCCTTAT CTTCCTGGT                                                   199
```

(2) INFORMATION FOR SEQ ID NO:15:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..303
        (D) OTHER INFORMATION: /standard_name="DB#122"

(xi) SEQUENCE DESCRIPTION: SEQ ID NO:15:

```
AGGGTGAGGT GGTATTTGAG GATTGGGGTT TTGAGGAGGT GGTGGGATGT GGTAAGGGGT      60
TGAGGCATAC TAAGGATTTT GTGCAGTCAA GTCTATTACT GAGTGATTCT AACCAGGAGT     120
GGATAGTGCG TTCTTAGCCT ATTCTATGTT TGAAGAGGGA AAGTGTTGTA GAGGCCTTCC     180
ATCAGTATTA GTGTTGGCAG TAAAACCTAA TGGAGGCAGA TCCTGTCTCT TTGCATTTCC     240
ATTCTCATCT CAGTGATCTG CTGCATTAAC TGTATAATCT GTTCATTCTG ATCTGCTATA     300
GTG                                                                    303
```

(2) INFORMATION FOR SEQ ID NO:16:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..196
        (D) OTHER INFORMATION: /standard_name="DB#124"

(xi) SEQUENCE DESCRIPTION: SEQ ID NO:16:

```
GAGGAGGATA TCCATTTGTG AGCAAAGCAT CAAACTTACA ATTGATTACA TAAGAAGCTA      60
```

TGTGTCAAAC TGCTGAATCT AAGAAAGTGG TACTCGATTG GGAGTTGAGG ATATGACAAT      120

GAATTAAACC TGTTAGATGT AAATCTGCCT AGTAATTCTA TGAATTACCG ATAGTTTGAA      180

TTGGACAAGT TAGACT      196

( 2 ) INFORMATION FOR SEQ ID NO:17:

( i ) SEQUENCE CHARACTERISTICS:
        ( A ) LENGTH: 272 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..272
        ( D ) OTHER INFORMATION: /standard_name="DB#131"

( x i ) SEQUENCE DESCRIPTION: SEQ ID NO:17:

CAAGGCTTCA CACTGAGCCA TGAAGTTCTT AGAAGTAGCC CCTTGTTGTT CAATGTTTAT      60

CACCTTCACC GCAACCATAC ATTCACCTGG ATCAAGTACC CCTTTGTAAA CAGAAATAAA      120

GCTACCATTT CCAATCAAAT TGGCAGAAGA GAATCCATTT GTCGCTCTAT ATAGGCTCTC      180

ATAAGTAACC GGTGAAGATG TTAAAGAAGG ATCTCCCTTG CCTTCCTTAA CCGAATGATT      240

ATGACTAAGC ATGATGAAAC CATGCACAGT CC      272

( 2 ) INFORMATION FOR SEQ ID NO:18:

( i ) SEQUENCE CHARACTERISTICS:
        ( A ) LENGTH: 164 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..164
        ( D ) OTHER INFORMATION: /standard_name="DB#132"

( x i ) SEQUENCE DESCRIPTION: SEQ ID NO:18:

GGGTCATGAC CGAATTGGCT CTAATTGGGG CTGATATTCA AGAGGTTATT GGAAGTGCTA      60

TTGCTATAAA GATTTTGAGT CGAGGGTTCT TGCCTCTATG GTCTGGTGTT GTCATCACTG      120

CTCTTGATTG CTTTGTATTC TTATTTCTTG AGAACTATGG ATGA      164

( 2 ) INFORMATION FOR SEQ ID NO:19:

( i ) SEQUENCE CHARACTERISTICS:
        ( A ) LENGTH: 348 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( x i ) FEATURE:
        ( A ) NAME/KEY: misc_feature
        ( B ) LOCATION: 1..348
        ( C ) OTHER INFORMATION: /standard_name="DB#133"

( x i ) SEQUENCE DESCRIPTION: SEQ ID NO:19:

| | | | | | |
|---|---|---|---|---|---|
| AGCAAGTCTA | TGAGTATCTT | ATTTAATTGT | AGTCTTAAGA | TTAAACATAA | ACTGGTGGTG | 60 |
| CACCAGCTGG | TCGTGTGGTG | AACGAGACTT | TGGATTTGTC | CATTATGCAG | AAAGGTCGAG | 120 |
| CGCTCTGAAA | GCTGTCAAAG | ACACTGAAAC | ATATGAAGTA | AATGGTCAGA | TGTTAGAAGT | 180 |
| AGTTCTTGCA | AAGCCTCAGA | CTGAAAAGAA | GTTGATGCA | GCTAGTCCTC | ACATGCGATG | 240 |
| CCACATCATA | TTATATTCCC | ATCCAGGCTA | TGGTGACTTC | CGATGACCGA | TGTCACCTAT | 300 |
| CTGCTGGTAT | GGTCGTCGTC | GTCGTCGTCG | TCCGCGTCGT | CACACACC | | 348 |

( 2 ) INFORMATION FOR SEQ ID NO:20:

( i ) SEQUENCE CHARACTERISTICS:
            ( A ) LENGTH: 239 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Lycopersicon esculentum cv 'Rutgers Large
                Red'

( i x ) FEATURE:
            ( A ) NAME/KEY: misc_feature
            ( B ) LOCATION: 1..239
            ( D ) OTHER INFORMATION: /standard_name="DB#134"

( x i ) SEQUENCE DESCRIPTION: SEQ ID NO:20:

| | | | | | |
|---|---|---|---|---|---|
| AACCCATCAA | AAAGTGTATT | TATATCTCAG | TGAACATATG | TTCAGCACTC | GTGCTGTCTG | 60 |
| ATCTAGGGCC | AAAACTGGCA | CAGGTACAAC | CTGCAATACC | TCATTACAAC | ATTTGAGAAA | 120 |
| TGAGCAAATA | ATACTTCCAC | ATTCAGCATA | AACAAAAGTT | ATCTTGACGT | TGATCTGTTT | 180 |
| AAGATGAGAT | GATGATCTGT | TTTTCTCAGC | CAATAGTGCT | CAGCATATCT | TCTTCATCA | 239 |

( 2 ) INFORMATION FOR SEQ ID NO:21:

( i ) SEQUENCE CHARACTERISTICS:
            ( A ) LENGTH: 255 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Lycopersicon esculentum cv 'Rutgers Large
                Red'

( i x ) FEATURE:
            ( A ) NAME/KEY: misc_feature
            ( B ) LOCATION: 1..255
            ( D ) OTHER INFORMATION: /standard_name="DB#136"

( x i ) SEQUENCE DESCRIPTION: SEQ ID NO:21:

| | | | | | |
|---|---|---|---|---|---|
| GGCAAACAAA | GTAGAATTAC | ATTGCAGTTT | CTCCCTTACT | AGTCATCAAA | TAAATATTCA | 60 |
| CAAATTGAAA | ACAGCTGTTC | CCTTAACAAC | CCTCATGAAG | GGAGATTAAG | AAGTAACTAA | 120 |
| GTTCTTTCAC | GGAATTTATT | CATTCACCCC | AAGCACAATA | AGACATTGCT | GTTACAAAAG | 180 |
| TCCCAGACGT | GCCTGGAGAC | AATTTGCGC | ATCATCCCAT | TGCATATTTC | TGAGTCCAGC | 240 |

ATCGAGCAGT GGTTC                                                                                              255

( 2 ) INFORMATION FOR SEQ ID NO:22:

( i ) SEQUENCE CHARACTERISTICS:
           ( A ) LENGTH: 283 base pairs
           ( B ) TYPE: nucleic acid
           ( C ) STRANDEDNESS: single
           ( D ) TOPOLOGY: linear ( i i ) MOLECULE TYPE: DNA (genomic)

( v i ) ORIGINAL SOURCE:
           ( A ) ORGANISM: Lycopersicon esculentum cv 'Rutgers Large
                Red'

( i x ) FEATURE:
           ( A ) NAME/KEY: misc_feature
           ( B ) LOCATION: 1..283
           ( D ) OTHER INFORMATION: /standard_name="DB#137"

( x i ) SEQUENCE DESCRIPTION: SEQ ID NO:22:

AATAATCCAA TAAAATACAG ATTGGAAGTT ACATTACAAT CCCAAATGAC ATGATATTAT        60

ACGTTCATCA AACAATCTAT CCACAAGAGA AAACAACCAA AAGCCAAGAA TAAATGGAAA       120

AAGTAGCTAG GTACTCCATT AGCGAAGTAG TAATAATATG GTCTTCAAAT ATCCACCATA       180

TGATGATCCA CTTGGTGAGG ACCAAATAGC ATAAATGATA CCAGGTAGCT ACCAAAGAGA       240

GTCAGCAAAC TGATGTTTTT GGCTATGGAA TCATGCTTGG AAT                         283

( 2 ) INFORMATION FOR SEQ ID NO:23:

( i ) SEQUENCE CHARACTERISTICS:
           ( A ) LENGTH: 243 base pairs
           ( B ) TYPE: nucleic acid
           ( C ) STRANDEDNESS: single
           ( D ) TOPOLOGY: linear ( i i ) MOLECULE TYPE: DNA (genomic)

( v i ) ORIGINAL SOURCE:
           ( A ) ORGANISM: Lycopersicon esculentum cv 'Rutgers Large
                Red'

( i x ) FEATURE:
           ( A ) NAME/KEY: misc_feature
           ( B ) LOCATION: 1..243
           ( D ) OTHER INFORMATION: /standard_name="DB#139"

( x i ) SEQUENCE DESCRIPTION: SEQ ID NO:23:

ATGAATTGTC CTACAACTGC ATTGCACAGA AGAGTACAAT TTTTTTTCTC TGAAATTTAT        60

TACACCTCAA GTAGTCCAAG TCCAGGCAGG ATCATCAGAT GTACAAAGAT TTGCTCAGTT       120

TTGTTCCTCC TAATCAATTC AAAGGATCTA ACTCAAAACT TGGCGTTGCA ATAGATAAAT       180

GCTGCTGGAT AATTAGGATA CAACATATCT AGTGTAATCC CACATAGGTC TGGAAGGGTG       240

GTT                                                                   243

( 2 ) INFORMATION FOR SEQ ID NO:24:

( i ) SEQUENCE CHARACTERISTICS:
           ( A ) LENGTH: 223 base pairs
           ( B ) TYPE: nucleic acid
           ( C ) STRANDEDNESS: single
           ( D ) TOPOLOGY: linear ( i i ) MOLECULE TYPE: DNA (genomic)

( v i ) ORIGINAL SOURCE:
           ( A ) ORGANISM: Lycopersicon esculentum cv 'Rutgers Large Red'

( i x ) FEATURE:
    ( A ) NAME/KEY: misc_feature
    ( B ) LOCATION: 1..223
    ( D ) OTHER INFORMATION: /standard_name="DB#140"

( x i ) SEQUENCE DESCRIPTION: SEQ ID NO:24:

| | | | | | | |
|---|---|---|---|---|---|---|
| GACTTGAGAA | CGTTAATATA | AAAGGTAAAT | GATTGTGGTT | AAAATAATTT | TACGTCTGGA | 60 |
| TAGCTTTTTA | TACAAGATTT | TGGAGTTGCT | TCTCCTTAAA | TCATATTAAG | GAAAGACACA | 120 |
| CCTCCAAAAC | ATTCTCTTGG | AAGAAATACC | AATTGAAACA | CATTACACAT | ACTGAGTTGA | 180 |
| GGGTCTTGTA | ATAGGCATCA | GTTAGGGTCA | GGATAACGAG | TTT | | 223 |

( 2 ) INFORMATION FOR SEQ ID NO:25:

( i ) SEQUENCE CHARACTERISTICS:
        ( A ) LENGTH: 163 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..163
        ( D ) OTHER INFORMATION: /standard_name="DB#141"

( x i ) SEQUENCE DESCRIPTION: SEQ ID NO:25:

| | | | | | | |
|---|---|---|---|---|---|---|
| GCTTATTTAT | GTCTGGTGTT | TCTTCTAAAC | CTTGGGTACT | TGCTGTAACC | CAGTACGGCA | 60 |
| GTACCTGCAG | TTTTTCTTTA | TCATATGATC | TTATTATGTG | GGACAGCAAA | CGGCCAGCCG | 120 |
| ACCGAAGCCG | GCGCTTCAAC | CAGGATCATC | TATGGAGGAA | TCT | | 163 |

( 2 ) INFORMATION FOR SEQ ID NO:26:

( i ) SEQUENCE CHARACTERISTICS:
        ( A ) LENGTH: 206 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..206
        ( D ) OTHER INFORMATION: /standard_name="DB#142"

( x i ) SEQUENCE DESCRIPTION: SEQ ID NO:26:

| | | | | | | |
|---|---|---|---|---|---|---|
| GTTCAGCCTA | CTCTATTGTT | GTTGGATGAA | CCTACAAATC | ATCTTGACCT | TCGGGCTGTT | 60 |
| CTATGGTTAG | AGGAGTACTT | GTGCAGATGG | AAGAAAACTT | TGGTCGTTGT | TTCGCATGAT | 120 |
| CGAGACTTTC | TGAACACTGT | TTGCGGTGAG | ATTATTCATC | TCCATGACAT | GAAACTACAC | 180 |
| TTCTATCGTG | GTAACTTTGA | GATTTT | | | | 206 |

( 2 ) INFORMATION FOR SEQ ID NO:27:

( i ) SEQUENCE CHARACTERISTICS:
        ( A ) LENGTH: 309 base pairs (B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Lycopersicon esculentum cv 'Rutgers Large Red'

(ix) FEATURE:
(A) NAME/KEY: misc_feature
(B) LOCATION: 1..309
(D) OTHER INFORMATION: /standard_name="DB#144"

(xi) SEQUENCE DESCRIPTION: SEQ ID NO:27:

| | | | | | | |
|---|---|---|---|---|---|---|
| AAGGGGGCAA | CACAATATCT | AGAATGAACA | AAACTTTAGA | TATTCGACAG | GATAAGAAAA | 60 |
| TGGTAAAGGA | ACATAATAGT | TCTACGAATT | CTCAAGTATC | TTCTAATCAT | CTAGGGGAA | 120 |
| GGGGCACATT | AACTCTTCCA | TCTTCAAGGT | CTTGGACGCT | CAAACCTGGA | GGAAGTGACT | 180 |
| GCTTCAACTT | GTCAGCCTTC | TCAAAGTCCA | GCACACAGAG | TGTGTAAAGG | TACTTGGAGC | 240 |
| CAGCGACCTT | GAACTTACCA | TATCCTTGTT | CTCTGATCTG | CAGTCGTGCA | TCCTCCTCCT | 300 |
| TGCTGTAGG | | | | | | 309 |

(2) INFORMATION FOR SEQ ID NO:28:

(i) SEQUENCE CHARACTERISTICS:
(A) LENGTH: 292 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Lycopersicon esculentum cv 'Rutgers Large Red'

(ix) FEATURE:
(A) NAME/KEY: misc_feature
(B) LOCATION: 1..292
(D) OTHER INFORMATION: /standard_name="DB#146"

(xi) SEQUENCE DESCRIPTION: SEQ ID NO:28:

| | | | | | | |
|---|---|---|---|---|---|---|
| GGTGTGAGTT | AGTTTTTTGT | GGTTTTCATG | AATGCCGTGT | CAAGGAGACC | TTAGATTTGT | 60 |
| GTTTTGACAG | TTTCATCGAG | TCTAAAGCAT | CGAGTATATT | GATTTGCTTA | TGCGGTTTGT | 120 |
| GTGTACCGGA | TTCCGAACGA | ATCCTGAGGG | TCCTCTTGAT | GTTTTGGAAG | TTGGCTGATT | 180 |
| TTTCTGGTGC | CTGAATCTAG | TGTGTCTCGC | GATCTCGAGC | CTCATTGTTG | CGAGGTAATG | 240 |
| TTCGCTTCGC | GAAGGGGTCA | AGTTCCTGAT | CTCACGTACA | CAAGAAGGAC | CT | 292 |

(2) INFORMATION FOR SEQ ID NO:29:

(i) SEQUENCE CHARACTERISTICS:
(A) LENGTH: 176 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Lycopersicon esculentum cv 'Rutgers Large Red'

(ix) FEATURE:
(A) NAME/KEY: misc_feature
(B) LOCATION: 1..176
(D) OTHER INFORMATION: /standard_name="DB#147"

( x i ) SEQUENCE DESCRIPTION: SEQ ID NO:29:

| | | | | | |
|---|---|---|---|---|---|
| GGCGCCCTAG | GCCACCATCC | TTCTTAAAGT | AAAGGAAGAA | AAGAGGAAGA | AGATTGCTAA | 60
| GAACTTGAAG | AAGTACAGCA | AGAAGTATGA | AGCAGAGGAT | CAGGATGTTT | CATTGCTGTT | 120
| GAGCGAGCAA | GACCGTGAGA | AGCGAAAGAA | GCTGAAAGAG | ATGGGAGCAT | GGATTA | 176

( 2 ) INFORMATION FOR SEQ ID NO:30:

( i ) SEQUENCE CHARACTERISTICS:
        ( A ) LENGTH: 184 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..184
        ( D ) OTHER INFORMATION: /standard_name="DB#148"

( x i ) SEQUENCE DESCRIPTION: SEQ ID NO:30:

| | | | | | |
|---|---|---|---|---|---|
| AAGATGATTA | AGCTAAATAT | CAAATAGAAA | CCAAATCCAT | AGGACATATA | TCTTTTTAAC | 60
| AGCAATAATT | CCAATCTAAC | AGATGAGAGG | TAATATTCCA | GAAAAAATA | TTCGAAACTT | 120
| CGATTCATCA | GCGAAATGAA | AGACATCAAA | CGAAACAGTG | TCAAAACTGC | TTCTTTAGAA | 180
| ACGT | | | | | | 184

( 2 ) INFORMATION FOR SEQ ID NO:31:

( i ) SEQUENCE CHARACTERISTICS:
        ( A ) LENGTH: 325 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..325
        ( D ) OTHER INFORMATION: /standard_name="DB#149"

( x i ) SEQUENCE DESCRIPTION: SEQ ID NO:31:

| | | | | | |
|---|---|---|---|---|---|
| ACCGTTCATT | TTGGAATCGT | AGCACAAAAC | CTTCTTTGGA | TCTCGCGAAG | GAGCTCCTAG | 60
| ATCTTTTTAG | TGCAAATAAA | ATGGCGAAAC | GCTTTTTTTT | TCACAAACAG | CGGATCAGAA | 120
| GCCAATGACA | CACAGGTGAA | ACTGGTATGG | TATTACACAT | GCACTCGGCC | AGACAAAAAG | 180
| AAATTTATTG | CTCGAACAAA | ATCATACCAC | GGATCCACCT | CTCATTTCCG | CTAGTCTCTC | 240
| TGTCTTCCTG | CACTACATCA | GCAATTCGAT | CTACCAGCTC | CGTTTGTCTG | CATACTGACT | 300
| GCCCTATTTG | GCGCTTCATC | AGCCA | | | | 325

( 2 ) INFORMATION FOR SEQ ID NO:32:

( i ) SEQUENCE CHARACTERISTICS:
        ( A ) LENGTH: 249 base pairs
        ( B ) TYPE: nucleic acid
        ( C ) STRANDEDNESS: single ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..249
    ( D ) OTHER INFORMATION: /standard_name="DB#151"

( x i ) SEQUENCE DESCRIPTION: SEQ ID NO:32:

| | | | | | |
|---|---|---|---|---|---|
| GGACTACAAA | CTTTTGATGC | TCTATTTCCC | TTGTAAGATA | CTTATAAGAA | CTACAATGTC | 60 |
| TTAACAAGGA | CAGTTTTGTT | CAAACTAAAT | ATCCTTGATC | CATCTGTCAT | GAAAGGATCT | 120 |
| GAAAATACCA | TTGATTCAGC | AAAAACTACA | CAAGGACAT | ATACTAGCAA | TAAAAGTTGC | 180 |
| AGGAACACAT | ACTGCCGTCA | AAGAGAGTTC | AGGCCAGCGA | CATTGTTCTA | TTAATCCTAC | 240 |
| TGGTATCCC | | | | | | 249 |

( 2 ) INFORMATION FOR SEQ ID NO:33:

( i ) SEQUENCE CHARACTERISTICS:
        ( A ) LENGTH: 211 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..211
        ( D ) OTHER INFORMATION: /standard_name="DB#152"

( x i ) SEQUENCE DESCRIPTION: SEQ ID NO:33:

| | | | | | |
|---|---|---|---|---|---|
| AACTTAAATG | AACTTCTAGC | TTAAGATAAA | CAGTTGAACA | TCACCAGATA | ACGAAAATAC | 60 |
| CGGCGAAACG | ATAGGAGTTT | AGTCAAGCCA | AAAGTATTAT | TATGGATAGC | AAATAATCAG | 120 |
| GACAGTGATC | TACTACTATG | TCTTTGCAAG | AAAAAACTGT | TGCTACAAAC | TATAATTACT | 180 |
| AACCGGTCTA | CATGTAGGGT | TGATAGGCTG | T | | | 211 |

( 2 ) INFORMATION FOR SEQ ID NO:34:

( i ) SEQUENCE CHARACTERISTICS:
        ( A ) LENGTH: 302 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..302
        ( C ) OTHER INFORMATION: /standard_name="DB#153"

( x i ) SEQUENCE DESCRIPTION: SEQ ID NO:34:

| | | | | | |
|---|---|---|---|---|---|
| GGTGGTATGA | TCTTTGCTTT | GGTTACTGT | ACTGCTGGTA | TCTCAGGAGG | ACACATTAAT | 60 |
| CCAGCTGTGA | CATTTGGTTT | GTTCTTGGCA | AGGAAGTTGT | CATTAACAAG | GGCAGTGTTT | 120 |

```
TATATAGTGA  TGCAGTGTCT  TGGTGCTATC  TGTGGTGCTG  GTGTTGTGAA  GGGTTTTATG     180

GTTGGACCCT  ATGAGAGACT  TGGTGGTGGT  GCTAATGTTG  TTAATCCTGG  TTACACCAAA     240

GGTGATGGAC  TTGGTGCTGA  GATTATTGGT  ACTTTGTCCT  TGTTTACACT  GTTTTCTCTG     300

CC                                                                        302
```

( 2 ) INFORMATION FOR SEQ ID NO:35:

( i ) SEQUENCE CHARACTERISTICS:
        ( A ) LENGTH: 243 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..243
        ( D ) OTHER INFORMATION: /standard_name="DB#154"

( x i ) SEQUENCE DESCRIPTION: SEQ ID NO:35:

```
GGATTAGGTG  ATAGATATGA  ACCCTAGAAA  TAGGGGATTT  TTGGCTAATT  CAATTGAAAG      60

ATTGATTAGA  GATCAAATTA  AGGAGATCGG  AGTATGTAAG  GCAAGCAGTG  CAAGAGGACA     120

ATGGTGGAAA  CTATGCAAAG  GCATTTCCGT  TGTATATGAA  TGCATCGGAG  TACTTCAAGA     180

CCCATTTGAA  GTACGAGAAG  AATCCTAAGA  TAAAGGAGGC  AATTACCCAG  AAATTTACTG     240

AGT                                                                       243
```

( 2 ) INFORMATION FOR SEQ ID NO:36:

( i ) SEQUENCE CHARACTERISTICS:
        ( A ) LENGTH: 272 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..272
        ( D ) OTHER INFORMATION: /standard_name="DB#155"

( x i ) SEQUENCE DESCRIPTION: SEQ ID NO:36:

```
GAGCTGATTA  AACCTTCCAG  TGATGGAAAT  GCTGGTCCTG  AGTTGGTTAA  AGGGAGTAGA      60

AAGTCACAGA  TGCGAGGAAG  ATGGAGAGGG  ATTGACCCAA  TATTATTTTA  CCACGAGGAG     120

ACAACAGTGG  GTCAGATAAA  GGCCTTCTAT  GGCATTAAGG  AATCCTTTCC  ATTCAAAGGT     180

CATTTGATTG  TGAGGAATAC  TGATATCGAC  CATGTGAAAA  GAGTTTATTA  TGTATCTAAA     240

TCTGTGAAAG  AAGTTCTTAA  ACTCAATTTT  GT                                    272
```

( 2 ) INFORMATION FOR SEQ ID NO:37:

( i ) SEQUENCE CHARACTERISTICS:
        ( A ) LENGTH: 279 base pairs
        ( B ) TYPE: nucleic acid
        ( C ) STRANDEDNESS: single (D) TOPOLOGY: linear (i i) MOLECULE TYPE: DNA (genomic)

(v i) ORIGINAL SOURCE:
    (A) ORGANISM: Lycopersicon esculentum cv 'Rutgers Large Red'

(i x) FEATURE:
    (A) NAME/KEY: misc_feature
    (B) LOCATION: 1..279
    (D) OTHER INFORMATION: /standard_name="DB#156"

(x i) SEQUENCE DESCRIPTION: SEQ ID NO:37:

| | | | | | |
|---|---|---|---|---|---|
| ACCAGAAATG | CAGATTGGAT | AGAGATGATT | CCACAAAGGG | AATCTTAATT | GAAACAAGAA | 60 |
| GATATCCTGT | GAATATATTT | ACAGATTGAG | ATAAGACTTC | TATAAAACCT | CAAAATTCCT | 120 |
| CAATCATCTG | ACACCTAGCT | TACTATTTTA | CCTGGTTCTG | TCAGCCTATT | TATACCAACA | 180 |
| AGACCTACAT | CTTAAGAAAT | TAGAGACAGA | TCCTAATAAT | TCATCTTCAT | ACATGTTATT | 240 |
| GACATTGCCG | CCATCTCGTG | ATTTATCCAA | GCAGCAACC | | | 279 |

(2) INFORMATION FOR SEQ ID NO:38:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (i i) MOLECULE TYPE: DNA (genomic)

(v i) ORIGINAL SOURCE:
        (A) ORGANISM: Lycopersicon esculentum cv 'Rutgers Large Red'

(i x) FEATURE:
        (A) NAME/KEY: misc_feature
        (B) LOCATION: 1..183
        (D) OTHER INFORMATION: /standard_name="DB#157"

(x i) SEQUENCE DESCRIPTION: SEQ ID NO:38:

| | | | | | |
|---|---|---|---|---|---|
| AGCTGGTAAC | AGAATGAACC | AAGGAAGAGA | GCAATTTCCA | GTCCATAAAT | AAAACTAGCA | 60 |
| TCAAAATGCC | CAACAGCAGA | GACCCTAGCT | GCCAATAAGA | CATCAATTTT | CTAATGTTTT | 120 |
| GCCTTAACTA | AATGTGCCTT | TCAGCTGTGA | CTTCAAAAAT | ACGAGACTCA | GGTTTCTTAT | 180 |
| GGG | | | | | | 183 |

(2) INFORMATION FOR SEQ ID NO:39:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (i i) MOLECULE TYPE: DNA (genomic)

(v i) ORIGINAL SOURCE:
        (A) ORGANISM: Lycopersicon esculentum cv 'Rutgers Large Red'

(i x) FEATURE:
        (A) NAME/KEY: misc_feature
        (B) LOCATION: 1..290
        (D) OTHER INFORMATION: /standard_name="DB#161"

(x i) SEQUENCE DESCRIPTION: SEQ ID NO:39:

| | | | | | |
|---|---|---|---|---|---|
| CGAGAGAGAT | CCCGGTCTAC | AACATCACAT | TAGAGAGGTA | TTCTCAAATA | TACAAAACAG | 60 |
| AAACACCCCT | CTATCTCTTG | AAAGTTTAGC | AAGTTTGTTA | AATTGCAAGA | ATCAGTGCAT | 120 |

```
GCTTGTTGAT  AAGTCCTTGA  AGATAGCTGC  TCAACTTGCT  GTTCAACTTG  GGGGTAGATA        180

TTAGACATTA  TATAGCCTCA  TTTCCTCTTC  GGTGCAATAG  TTAGTAACTC  AAAGCTCCTA        240

AGAGCATCAT  CCCTACCCCT  CTAGTTGGCA  GGTAGCCGCG  GTAAGAGTAG                    290
```

( 2 ) INFORMATION FOR SEQ ID NO:40:

( i ) SEQUENCE CHARACTERISTICS:
        ( A ) LENGTH: 279 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..279
        ( D ) OTHER INFORMATION: /standard_name="DB#163"

( x i ) SEQUENCE DESCRIPTION: SEQ ID NO:40:

```
GGGGAAAGGC  GAATGTCAAA  CTGGCAAACA  AAGTAGAATT  ACATTGCAGT  TTCTCCCTTA         60

CTAGTCATCA  AATAAATATT  CACAAATTGA  AAACAGCTGT  TCCCTTAACA  ACCCTCGATG        120

AAGGGAGATT  AAGAAGTAAC  TAAGTTCTTT  CACGGAATTT  ATTCATTCAC  CCCAAGCACA        180

ATAAGACATT  GCTGTTACAA  AAGTCCCAGA  CATGCCTGGA  GACAATTTTG  CGCATCATCC        240

ATTGCATATT  TCTGAGTCCA  GCTACGAGCA  GTGGTTTCC                                 279
```

( 2 ) INFORMATION FOR SEQ ID NO:41:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..172
        ( D ) OTHER INFORMATION: /standard_name="DB#164"

( x i ) SEQUENCE DESCRIPTION: SEQ ID NO:41:

```
GCATGGACAA  TATCGCCGAC  TGGCGGTCAT  TCACAGGGAA  CTTTTACAGG  ACCCAAGAGT         60

TAATTGGTCA  GGCTCCAGTC  TTCGAACTGA  GGCTACTGGC  TACGGATTGG  TTTTCTTTGC        120

TCAACTTATG  CTTGCAGACA  TGAACAAAGA  ACTAAAAGGA  TTAAGGTGTG  CA                172
```

( 2 ) INFORMATION FOR SEQ ID NO:42:

( i ) SEQUENCE CHARACTERISTICS:
        ( A ) LENGTH: 155 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
    ( A ) NAME/KEY: misc_feature
    ( B ) LOCATION: 1..155
    ( D ) OTHER INFORMATION: /standard_name="DB#165"

( x i ) SEQUENCE DESCRIPTION: SEQ ID NO:42:

| | | | | | |
|---|---|---|---|---|---|
| AAGGAAAGTT | TATGCCCCTA | TGGGAGCTTT | TCGACTGCAG | AAACTCACTC | AAATTAGTAA | 60
| TTGAAAATGC | ATAGCAAGAC | AATATCTCAC | AGGCCACATA | TAGGCCATAA | TAACATGTAG | 120
| TATGTCTTAT | TTAAAGAGGC | GAACATTAGA | ACACT | | | 155

( 2 ) INFORMATION FOR SEQ ID NO:43:

( i ) SEQUENCE CHARACTERISTICS:
        ( A ) LENGTH: 262 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..262
        ( D ) OTHER INFORMATION: /standard_name="DB#166"

( x i ) SEQUENCE DESCRIPTION: SEQ ID NO:43:

| | | | | | |
|---|---|---|---|---|---|
| AGCAGCTCAA | GTGGCATGTG | TAATCTCAAT | GTTAATAGTC | ACTTATAGTA | CTGATTGGGA | 60
| AGGAGCATCC | TTGAAGGCAA | AACAACTAGT | GGGAAGAACT | AATGAACTCC | CATATGAAGA | 120
| TCAACTGGTA | AAAATTGAGG | AGGGTAATGG | ATTTCTCAAC | GATTAGCTT | CTGAAGTGGA | 180
| AGGAATCTAA | GGATGCAATG | GATGCAAGGA | AAAGGAAGAG | ATGGCCACAG | CAGAGAACAA | 240
| GACATTACAT | TCTCTCAGTA | TT | | | | 262

( 2 ) INFORMATION FOR SEQ ID NO:44:

( i ) SEQUENCE CHARACTERISTICS:
        ( A ) LENGTH: 193 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..193
        ( D ) OTHER INFORMATION: /standard_name="DB#168"

( x i ) SEQUENCE DESCRIPTION: SEQ ID NO:44:

| | | | | | |
|---|---|---|---|---|---|
| GGTGTTGATG | GTCCAGACGT | GCCTGTTGGT | GCTGGTGTTG | ATGGTCCTAG | GCTGACAGTT | 60
| GGGTTACCAG | TAGGTTCAAT | TGTAGATTCG | GGTGTGCCTG | TAGGTGCGGT | CGTAGCTTCA | 120
| GGAGTTCCTG | TTGGTGCTGG | TGTTGATGGC | CCAGGAGTGC | CTGTAGGTGC | GGTTGTAGCT | 180
| TCAGGAGGTT | CCT | | | | | 193

( 2 ) INFORMATION FOR SEQ ID NO:45:

( i ) SEQUENCE CHARACTERISTICS:
    ( A ) LENGTH: 206 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..206
    ( D ) OTHER INFORMATION: /standard_name="DB#169"

( x i ) SEQUENCE DESCRIPTION: SEQ ID NO:45:

```
GAACGCTTAT AAAGGTGTTG GCATTGTTTT AGTTACTATT TCCAGTTATT GTCCCTTTCC      60
AGCAGAATAT GTTGTCTTCT TCAGGAAATG CAGATATTCC TGAGTCACCA CTCATCATTA     120
GAGCCATCAA CTCAGATTGC AACCTTTTAA GAACAGACTG AGTATCAACC GTCTTCACAG     180
TAGTCTGTGT CTGCTTTGGT GAAGGT                                          206
```

( 2 ) INFORMATION FOR SEQ ID NO:46:

( i ) SEQUENCE CHARACTERISTICS:
    ( A ) LENGTH: 318 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..318
    ( D ) OTHER INFORMATION: /standard_name="DB#172"

( x i ) SEQUENCE DESCRIPTION: SEQ ID NO:46:

```
AAGGGGGCAA CACAATATCT AGAATGAACA AAACTTTAGA TATTCGACAG GATAAGAAAA      60
TGGTAAAGGA ACATAATAGT TCTACGAATT CTCAAGTATC TTCTAATCAA TCTAGGGGGA     120
AGGGACACA  TTAACTCTTC CATCTTCACA GGTCTTGGAC GCTCAAACCT GGAGGAAGTG     180
ACTGCTTCAA CTTGTCAGCC TTCTCAAAGT CAGACACACA GAGTGTGTAA AGGATCTGGA     240
GACGCGAACC TTGAACTTAA CCATATCCTT GTTCTTCTTG ATCTTGACAG ATCGTGCATC     300
TTCCTCCTTG CTGTAAGA                                                   318
```

( 2 ) INFORMATION FOR SEQ ID NO:47:

( i ) SEQUENCE CHARACTERISTICS:
    ( A ) LENGTH: 239 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..239
    ( D ) OTHER INFORMATION: /standard_name="DB#173"

( x i ) SEQUENCE DESCRIPTION: SEQ ID NO:47:

| | | | | | |
|---|---|---|---|---|---|
| CCTTCTTGCT | ACTATTGCCT | TTTGCAGTAG | TATGCAAGAG | GCAATAGTAG | CAAGAAGCAG | 60
| AGCTGAAGCC | CCAACTGATG | ATCCTATAAT | GATTTCTTA | CGGCTGCGAT | TGGTTTCCCC | 120
| TTCGTGAAGA | TTAAAGTTTC | CAGTATAATT | CAAAATCACA | CCGTTATCAC | GAAGACCAGA | 180
| TGTCCCAACT | TACAGATAAT | ACATCTTGAG | AACAATCAGT | TGAGACATCG | CTAAATCGG | 239

( 2 ) INFORMATION FOR SEQ ID NO:48:

( i ) SEQUENCE CHARACTERISTICS:
        ( A ) LENGTH: 224 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..224
        ( D ) OTHER INFORMATION: /standard_name="DB#175"

( x i ) SEQUENCE DESCRIPTION: SEQ ID NO:48:

| | | | | | |
|---|---|---|---|---|---|
| ACATCCCCCG | GAATTCATTC | TTCCATAATA | GGAAGAGTAT | CTTGTAAAGG | AAATCTCAAA | 60
| TTGTAAAATT | GACTGCCTTG | CCGGACGTAC | TAAGTTTAGC | TATAACATCT | TTTAGAAACC | 120
| TGCCCATCCA | GCAGGTTGGG | ACGCTGATTT | GCTATCAATA | TTCTTTGGTT | CACCAAATGC | 180
| TGAGAATTTT | TCGACTCATT | GAGAGTGGCC | TTTATCTGAG | AGCT | | 224

( 2 ) INFORMATION FOR SEQ ID NO:49:

( i ) SEQUENCE CHARACTERISTICS:
        ( A ) LENGTH: 186 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..186
        ( C ) OTHER INFORMATION: /standard_name="DB#176"

( x i ) SEQUENCE DESCRIPTION: SEQ ID NO:49:

| | | | | | |
|---|---|---|---|---|---|
| GCCCGGCTCG | GAATATTAAG | TTTTAACTAG | AAAATTAAAG | TCCAAGTGAT | TTCAACATCT | 60
| GATTTCAAAA | TTTGAAACAA | CCACCGAGTC | TAAGATGGCA | CGAATCTAAG | AGAAGCTTGA | 120
| ACTAGTAGGT | GCACCGCCGC | CAAAACCTCC | AGTCCAGGCC | GAATCCAGGT | CTTCCACAGA | 180
| ACCCCT | | | | | | 186

( 2 ) INFORMATION FOR SEQ ID NO:50:

( i ) SEQUENCE CHARACTERISTICS:
        ( A ) LENGTH: 253 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..253
    ( D ) OTHER INFORMATION: /standard_name="DB#177"

( x i ) SEQUENCE DESCRIPTION: SEQ ID NO:50:

| | | | | | | |
|---|---|---|---|---|---|---|
| GGCGGTGGGT | TTGGTGACGA | CCAATGGTGG | CAGCGAGCTG | ATGGACCTCG | AAAAAAGTG | 6 0 |
| ACGGTTTTTG | GACGGTGTTT | GGTCGGAAAA | GGAAAAGGGT | CGTTCGGGGT | TTCTTTTGGA | 1 2 0 |
| GTGAATCTGG | TGGTTGTTAG | GTCCTGCTAA | GGTCACGAGC | TCATCGGCTG | AACTCTGCTT | 1 8 0 |
| TTCTGCTTCA | CCGGAGAAGA | TGAAACAATG | AGAAACATT | GAATTAGAAC | TATGGAGAAG | 2 4 0 |
| AAAGTCTGGG | TGA | | | | | 2 5 3 |

( 2 ) INFORMATION FOR SEQ ID NO:51:

( i ) SEQUENCE CHARACTERISTICS:
        ( A ) LENGTH: 318 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..318
        ( D ) OTHER INFORMATION: /standard_name="DB#178"

( x i ) SEQUENCE DESCRIPTION: SEQ ID NO:51:

| | | | | | | |
|---|---|---|---|---|---|---|
| GATGCCTCTA | GATCTGGTGC | ACCTGTTAAA | AACATAGGTG | AGAATCTGCT | TATAGCTCGA | 6 0 |
| GCATGGCATT | GCTTAAATGT | GGATGATGAG | GCTAATCGTG | GTAGCAGCTG | CTGTGAATAG | 1 2 0 |
| AAGGGCTTTT | GATGCCTCTA | GATCTGGTGC | CACCTGTTAA | AACATAGGTG | AGAATCTGCT | 1 8 0 |
| TATAGTCGAG | CATGGCATTG | CTTAAATGTG | GATGATATTT | TGGACAAGTC | ACAGAAGGAC | 2 4 0 |
| CAGGCTCAAC | CTACATTTGC | TCCTGGTGCT | CCTCACCAGC | CATGATATCC | GTCAAGTGTG | 3 0 0 |
| ATAACCTGGA | ATCACCTA | | | | | 3 1 8 |

( 2 ) INFORMATION FOR SEQ ID NO:52:

( i ) SEQUENCE CHARACTERISTICS:
        ( A ) LENGTH: 298 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..298
        ( D ) OTHER INFORMATION: /standard_name="DB#179"

( x i ) SEQUENCE DESCRIPTION: SEQ ID NO:52:

| | | | | | | |
|---|---|---|---|---|---|---|
| GGACTACAAA | CTTTTGATGC | TCTATTTCCC | TTGTAAGATA | CTTATAAGAA | CTACAATGTC | 6 0 |

```
TTAACAAGGA  CAGTTTTGTT  CAAACTAAAT  ATCCTTGATC  CATCTGTCAT  GAAAGGATCT       120

GAAAATACCA  TTGATTCAGC  AAAAACTACA  CAAAGGACAT  ATACTAGCAA  TAAAAGTTGC       180

AGGAACACAT  ACTGCCGTCA  AAAGAGAGTT  CAGGCCAGCG  ACAATTGTTC  TATTAATCCT       240

ACTGGTATCC  CTAGAAGTTA  ACTGTAGACA  ATCCAGAGTC  TGACCACATG  TTCTCAGA        298
```

( 2 ) INFORMATION FOR SEQ ID NO:53:

( i ) SEQUENCE CHARACTERISTICS:
        ( A ) LENGTH: 233 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..233
        ( D ) OTHER INFORMATION: /standard_name="DB#181"

( x i ) SEQUENCE DESCRIPTION: SEQ ID NO:53:

```
GAAGTGGCGT  TGGAGGATGA  GATAGAGGTG  GGACAAGTTG  ATTGTGGTAC  AGATAAGCCA       60

GTTTGTAATA  AAGCATTACA  ACAGCTTTTT  GTACATGATA  ATCAAACATT  AATGAACTTC       120

ATTGTCAATC  ATAGCAAAGT  AACCAATACT  GAAATAAGAC  AGCTATAGCC  AATAGGCCAA       180

GGTGTTCCTC  AGTTTCCACT  CTTGAATGGA  ATGGCTCTTA  TGATAACTTG  GTG             233
```

( 2 ) INFORMATION FOR SEQ ID NO:54:

( i ) SEQUENCE CHARACTERISTICS:
        ( A ) LENGTH: 258 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..258
        ( D ) OTHER INFORMATION: /standard_name="DB#182"

( x i ) SEQUENCE DESCRIPTION: SEQ ID NO:54:

```
CATTGGATTG  TTACAGGCTA  GAGAACTTGT  TAGTGCCCTA  CCTGGGATGT  TCCCTGGTAG       60

CTTGATGCCT  GTACTTCTTC  AAGCTGCTGT  ACATGTGAGA  GAGAACAAGG  CTGCTAAAGC       120

TGAAGAAATA  TTGGACAGTA  TGTAGATAAG  TTTCCTGACA  GGTCCAAGGT  TATCCTGCTT       180

GCAAGGGCTC  AGGTTGCTGC  AGCTGCTGGC  CATCCGAGAT  TGCAGCTGAT  TCCTTGGCGA       240

AAATACCTAG  ATTCAACA                                                        258
```

( 2 ) INFORMATION FOR SEQ ID NO:55:

( i ) SEQUENCE CHARACTERISTICS:
        ( A ) LENGTH: 302 base pairs
        ( B ) TYPE: nucleic acid
        ( C ) STRANDEDNESS: single
        ( D ) TOPOLOGY: linear (ii) MOLECULE TYPE: DNA (genomic)

(vi) ORIGINAL SOURCE:
    (A) ORGANISM: Lycopersicon esculentum cv 'Rutgers Large Red'

(ix) FEATURE:
    (A) NAME/KEY: misc_feature
    (B) LOCATION: 1..302
    (D) OTHER INFORMATION: /standard_name="DB#183"

(xi) SEQUENCE DESCRIPTION: SEQ ID NO:55:

| | | | | | | |
|---|---|---|---|---|---|---|
| GGGGGTGGGG | AGGAAGCAGA | CTTCCGGAAG | GAGGGGAAA | GAACTCTTAC | ACTATCTTGG | 60 |
| TTTTCCCTGT | ACCAATCCTC | TCTTTTTCGC | CCATCAAAGT | TTGGCGTATA | TTCAGTCTTA | 120 |
| ACATCCTCAA | TTTGTCTACT | TCTTGGTAGT | TTGTCAGTTC | CGGTGTTTTA | TTGTATTCCA | 180 |
| AAGTTCTAAG | TTACCTTGGC | TTAAGTGCAA | ACTTTAGTTT | CTGTAGTAGT | TACTATTTGT | 240 |
| TTGTGATTTG | CTAGACATTC | TTTCTCGAGG | CATATTTGTT | GGTGATAAGC | AGGTGTGCCA | 300 |
| CA | | | | | | 302 |

(2) INFORMATION FOR SEQ ID NO:56:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..288
        (D) OTHER INFORMATION: /standard_name="DB#187"

(xi) SEQUENCE DESCRIPTION: SEQ ID NO:56:

| | | | | | | |
|---|---|---|---|---|---|---|
| ACCAGAAATG | CAGATTGATA | GAGATGATTC | CACAAAGGGA | ATCTTAATTG | AAACAAGAAG | 60 |
| ATATCCTGTG | AATATATTTA | CAGATTGAGA | TAAGACTTCT | ATAAACCTC | AAAATTCCTC | 120 |
| AATCATCTGA | CACCTAGCTT | ACTATTTTAC | CTGGCTTCTG | TCAGCCTATT | TATACCAACA | 180 |
| AGACCTACAT | CTTAAGAAAT | TAGAGACAGA | TCCTAATAAT | TCATCTCACT | ACATGTTATT | 240 |
| GACATTGCGC | CATCTCGTGA | TTTTATCCAA | AGCAGCAACC | TTAGCTCG | | 288 |

(2) INFORMATION FOR SEQ ID NO:57:

(i) SEQUENCE CHARACTERISTICS:
        (A) LENGTH: 245 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..245
        (D) OTHER INFORMATION: /standard_name="DB#197"

(xi) SEQUENCE DESCRIPTION: SEQ ID NO:57:

| | | | | | | |
|---|---|---|---|---|---|---|
| GGATGGAATC | ACAAAAACAT | AATTTACTGA | AACCATCCCA | AAAATTGGCA | TAGGTATAAT | 60 |

```
AAATATATTG  AGGTTAAAAT  TGTCAAAATT  TGAAGCGCTA  ACGACTAACA  AATGAAGATT      120

CAGTATCGTA  GTAGAGGGTT  GCTGTGAGGC  GAGGGAGGAG  ATCCTTGTGT  GAGTGAGATT      180

TGCTTGAATC  GATGGACAAT  AAAAACTCAT  ACAGCTCTTA  TAGATCATTC  ATGTCACCTA      240

CCTAA                                                                      245
```

( 2 ) INFORMATION FOR SEQ ID NO:58:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..153
        ( D ) OTHER INFORMATION: /standard_name="DB#198"

( x i ) SEQUENCE DESCRIPTION: SEQ ID NO:58:

```
AAGGAAAGTT  TATGCCCCTA  TGGAGCTTTT  CGACTGCAGA  AACTCACTCA  AATTAGTAAT      60

TGAAAATGCA  TAGCAAGACA  ATATCTCACA  GGCCACATAT  AGGCCATAAT  ACATGTAGTA      120

TGTCTTATTT  AAAGAGACGA  ACATTAGAAC  ACT                                    153
```

( 2 ) INFORMATION FOR SEQ ID NO:59:

( i ) SEQUENCE CHARACTERISTICS:
        ( A ) LENGTH: 239 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..239
        ( D ) OTHER INFORMATION: /standard_name="DB#199"

( x i ) SEQUENCE DESCRIPTION: SEQ ID NO:59:

```
AGTGTTGGAG  AATCAATCTG  TAGAATACCG  CTTACGGATT  TCCATTAGAT  TTGACCCAGT      60

TAATGGTAGA  GGAACGAGGC  TTGGTTGTTG  ATGTTGATGG  TTTTAATGTT  GCTATGGATG      120

CTGCCAGGGA  AAGATCAAGA  AATGCTCAGA  GCAAGAATGC  CAGTGGTGCT  ATTGCCATGG      180

ATGCTGACGC  ATCTGCAGCA  TTGCACAAGA  AGTATCATTT  GTTGCAGCGA  CCCTTCTTG      239
```

( 2 ) INFORMATION FOR SEQ ID NO:60:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
    ( A ) NAME/KEY: misc_feature
    ( B ) LOCATION: 1..278
    ( D ) OTHER INFORMATION: /standard_name="DB#201"

( x i ) SEQUENCE DESCRIPTION: SEQ ID NO:60:

| | | | | | |
|---|---|---|---|---|---|
| CGTCAATCGT | TAATTGGATT | CAATATGAGT | GGCTGGGTTG | CTTACATCCA | ATCTTTGACT | 60 |
| GACAGCTGCA | ATGTTATCTC | CAGAGCGGCT | ATTGTTGGAC | TTAATGATGG | AGGTAGTGTT | 120 |
| TGGGCTCGAA | CGGAAGGCGA | CAAAGAATTA | AGGCTACCGT | GTCGGAACTC | AAGAAGTTTG | 180 |
| TTGAACTCTT | TGACAATCTT | GATAGTGTTC | CAGGAACTGC | CGCAGATCTA | GAAGGTGTTC | 240 |
| ACTACATTGT | ACCGAGAACT | GAGGAGAACC | TCATTTTT   |            |            | 278 |

( 2 ) INFORMATION FOR SEQ ID NO:61:

( i ) SEQUENCE CHARACTERISTICS:
        ( A ) LENGTH: 261 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..261
        ( D ) OTHER INFORMATION: /standard_name="DB#203"

( x i ) SEQUENCE DESCRIPTION: SEQ ID NO:61:

| | | | | | |
|---|---|---|---|---|---|
| GAAGCCAGAA | ATCGATGTTT | GATACATGTC | TGGCATTGTC | ACAGGTGAAT | GGGAACTAAT | 60 |
| ATGACTTTAC | ATCAACAAGA | AAAATGTAAA | CGCAGCAGGA | GCAGTTACAG | CTTTGCTAGA | 120 |
| AGAAGAAGCA | TTTTCTCTAA | TAGAAACAGT | AAATATTAGC | AAATAGAAGG | CAAAGGTGCA | 180 |
| GAATGTTTAC | AGCATTACAG | TTGAGCTAAA | TTCGAAATAC | AGGTTTGATT | CTTCTATGCC | 240 |
| CCGTCTGACT | GACAAAGTTG | G          |            |            |            | 261 |

( 2 ) INFORMATION FOR SEQ ID NO:62:

( i ) SEQUENCE CHARACTERISTICS:
        ( A ) LENGTH: 178 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..178
        ( D ) OTHER INFORMATION: /standard_name="DB#205"

( x i ) SEQUENCE DESCRIPTION: SEQ ID NO:62:

| | | | | | |
|---|---|---|---|---|---|
| AAACGTTTTA | AAAAGTTTTG | GAATTAAGTT | TTCAACAGCA | ATTTCACTAC | ATTAATCTGG | 60 |
| TCAAAGTAAT | ACATTAATAA | CTTATTAAAA | CTCTCCTAAA | ATTCTCATAC | TGAACAACTA | 120 |
| CATATTCCTC | ATAAGTCATA | TATTTCATTC | CTCTTCCAGT | TAGTTTTCTT | CTTCACGA   | 178 |

( 2 ) INFORMATION FOR SEQ ID NO:63:

( i ) SEQUENCE CHARACTERISTICS:
        ( A ) LENGTH: 244 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..244
        ( D ) OTHER INFORMATION: /standard_name="DB#207"

( x i ) SEQUENCE DESCRIPTION: SEQ ID NO:63:

| | | | | | | |
|---|---|---|---|---|---|---|
| AATCTAAGCT | CCAAGAACTA | GTCCATAGTT | TTTTTTTCTG | TGTGCCCTAA | AGACCATAAC | 60 |
| TTAGAGCCCA | AATCTTTTTC | TACATCAGCA | AAACAACGAT | TTGGTGTACC | AAACTGTTTG | 120 |
| GAACTCGGAC | CATTGATGCT | AATCATTCCA | AGCTGGTGTA | GAATTTACGC | ATTGGCTGCT | 180 |
| GGTTGTAATG | GCTCTTCTCT | TTCTTCTTGC | TGCAGCAAGC | CTGGCACTCC | CTGCAGCAGC | 240 |
| CTCT | | | | | | 244 |

( 2 ) INFORMATION FOR SEQ ID NO:64:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..278
        ( D ) OTHER INFORMATION: /standard_name="DB#208"

( x i ) SEQUENCE DESCRIPTION: SEQ ID NO:64:

| | | | | | | |
|---|---|---|---|---|---|---|
| ATTTCAAGGT | AGGTAATCCA | ATACAAAGCT | AATATTTGAA | GGAACTGTGT | TTGCAGTTAA | 60 |
| AGACAACTAC | AAATAAATGT | TCATGTTCAT | GGATGGGTTC | GGGTAGAGTA | TTTTTCAGAA | 120 |
| ATAGCAGAGG | CGAGAGTGTT | GCTATTGTTA | AGCCACAGAT | GAAGAACCAT | TTGCGCCAAA | 180 |
| CAATCCTAAA | GGATTTGTGG | GCAAGCTCTT | GGGCAGCCAG | GCTTAAACGA | TCAGTCAGAG | 240 |
| TTGGGAAACA | GGGTAAGCGG | CCGCATGACA | TGCTTGAG | | | 278 |

( 2 ) INFORMATION FOR SEQ ID NO:65:

( i ) SEQUENCE CHARACTERISTICS:
        ( A ) LENGTH: 155 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature ( B ) LOCATION: 1..155
( D ) OTHER INFORMATION: /standard_name="DB#209"

( x i ) SEQUENCE DESCRIPTION: SEQ ID NO:65:

| | | | | | |
|---|---|---|---|---|---|
| AAGGAAAGTT | TATGCCCCTA | TGGGAGCTTT | TCGACTGCAG | AAACTCACTC | AAATTAGTAA | 60
| TTGAAAATGC | ATAGCAAGAC | AATATCTCAC | AGGCCACATA | TAGGCCATAA | TAACATGTAG | 120
| TATGTCTTAT | TTAAAGAGAC | GAACATTAGA | ACACT | | | 155

( 2 ) INFORMATION FOR SEQ ID NO:66:

( i ) SEQUENCE CHARACTERISTICS:
        ( A ) LENGTH: 312 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..312
        ( D ) OTHER INFORMATION: /standard_name="DB#210"

( x i ) SEQUENCE DESCRIPTION: SEQ ID NO:66:

| | | | | | |
|---|---|---|---|---|---|
| AGCAGAGCCG | AATTAAGAAT | TAGAAGATGA | AAGCATATGC | AATTGCACTC | ATTGTCTGTG | 60
| GATCTGTTGC | AGCAGCTCTA | GTTTAATAT | CGTGTTGTTT | TTACAAAATT | GGCCGAAAGA | 120
| AAAAGAGTTC | CCCAGTGACT | CGGTATGTGA | CCAGTGGTTC | TCCGGTTATT | CCTCTGCCGC | 180
| CGAAGCCTTT | ACCAGCAAAT | CGTGATGTTG | AAAGGGCGAA | ATTAAACCAA | GACAATACAG | 240
| CAATGAGAGA | TGGTGGAATG | GTAATTCTAG | GTGCGGCTGC | TGCTGCAACA | GTTGTCACGC | 300
| GTGTTATCGA | CA | | | | | 312

( 2 ) INFORMATION FOR SEQ ID NO:67:

( i ) SEQUENCE CHARACTERISTICS:
        ( A ) LENGTH: 186 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..186
        ( D ) OTHER INFORMATION: /standard_name="DB#212"

( x i ) SEQUENCE DESCRIPTION: SEQ ID NO:67:

| | | | | | |
|---|---|---|---|---|---|
| GCCCGGCTCG | GAATATTAAG | TTTTAACTAG | AAAATTAAAG | TCCAAGTGAT | TTCAACATCT | 60
| GATTTCAAAA | TTTGAAACAA | CCACCAAGTC | TAAGATGGCA | CGAATCTAAG | AGAAGCTTGA | 120
| ACTAGTAGGT | GCACCGCCGC | CAAAACCTCC | AGATCCAGGC | CGAATCCAGG | TCTTCCACAG | 180
| AACCCT | | | | | | 186

( 2 ) INFORMATION FOR SEQ ID NO:68:

( i ) SEQUENCE CHARACTERISTICS:
        ( A ) LENGTH: 189 base pairs ( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..189
    ( D ) OTHER INFORMATION: /standard_name="DB#214"

( x i ) SEQUENCE DESCRIPTION: SEQ ID NO:68:

```
GCAGTCACAG GAATATATAC TTGAGACTGG GTCTGCAAGG AAATGTTATT GCCCGAACTG        60
ATAGGACGGA TGCTTGTTAT GGGCAATGAA CTTCCTGAAC CATTGACACC ATTTGAACAG       120
TCTTCTTCGG TGGACTCACC GGACTTAGAT GTCGGAGAAT GTGACGCTTC AGATCCCATG       180
TAAAACCTA                                                               189
```

( 2 ) INFORMATION FOR SEQ ID NO:69:

( i ) SEQUENCE CHARACTERISTICS:
        ( A ) LENGTH: 290 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..290
        ( D ) OTHER INFORMATION: /standard_name="DB#215"

( x i ) SEQUENCE DESCRIPTION: SEQ ID NO:69:

```
CTGGAGAACA GTTTAATGAA TATTTTCATT TAGCTCTCAC GTTCATTCTC ATTTACCGAA        60
GCAAAGAGAA TTTTATCAAA ATGGTTCACT GTACATGTAA AGAAACACGC CTATACAAGT       120
GTAAAATTGT TGCTGAACAT GTGAAAACAT ATGTACAAAA CCTATCCTGC ATTCCATGTG       180
GTGCTGTCCG CACCATGGGC ACAACAGAAA CAGTCTACAC GGAGTGCGGC ATAGAGAGGG       240
AGAGCGCATA TGGTCGCGTG AGAGGACCAG CCACACGACT GAGCAGCCTG                  290
```

( 2 ) INFORMATION FOR SEQ ID NO:70:

( i ) SEQUENCE CHARACTERISTICS:
        ( A ) LENGTH: 238 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..238
        ( D ) OTHER INFORMATION: /standard_name="DB#216"

( x i ) SEQUENCE DESCRIPTION: SEQ ID NO:70:

```
AGAGTAAAGG CAAAGGGTTG TTATTCTGTA AGGTATTCAC TAAATCTCAG TTACTGCAGT        60
```

5,612,471

77                                                                                       78

-continued

| | | | | | | |
|---|---|---|---|---|---|---|
| ATAAATAGAT | GATGGAGGAA | ACACTGCTAG | CTACATAATT | GATCCCCTCC | CTATTCTCAT | 120 |
| TTCTTGTTCA | ATGTATTACC | AATGTCTAGC | ACAAACGAT | ATTTCACGTC | CGATTTCAAA | 180 |
| AGACGTTCCA | ACGCGGTGTT | AACGTACTCA | TTGGCACCAT | TCAATATCTG | GTGTTATG | 238 |

( 2 ) INFORMATION FOR SEQ ID NO:71:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..260
        ( D ) OTHER INFORMATION: /standard_name="DB#217"

( x i ) SEQUENCE DESCRIPTION: SEQ ID NO:71:

| | | | | | | |
|---|---|---|---|---|---|---|
| AAGAGGCTAC | AAAATACATC | AAACTTTATA | GTAAAACATT | CTTAGAAGTC | CAAAAATCAC | 60 |
| TAGTAAATTC | CTGGGATAAC | TCTGTAAGGA | ACCTTTTCAC | AATACAATTT | CCAGTACTTG | 120 |
| CCATACTTTG | CCTTGCATCG | GTCATCGTCC | CTTTTAGCTC | GATCGAGAAG | GAGGATTATT | 180 |
| AGAAAGATGA | CGTAGAAGTA | GGGAATGAGT | GGTTGAAAAG | AGCTGGTACA | CTCAGAAAAT | 240 |
| GCCGTAATAT | TTCTGGACTA | | | | | 260 |

( 2 ) INFORMATION FOR SEQ ID NO:72:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..124
        ( D ) OTHER INFORMATION: /standard_name="DB#218"

( x i ) SEQUENCE DESCRIPTION: SEQ ID NO:72:

| | | | | | | |
|---|---|---|---|---|---|---|
| AAGACCCCAA | CAGAGAATTT | AGTTGTTATT | TGAGGTTGAA | ACGAAAGCTA | AACGCATTCT | 60 |
| TAGCAACTAC | CACTTCCTCC | CCCTAAAATA | AAATAAAACC | CAGCATTTTC | GAGGTGGTCC | 120 |
| TAAC | | | | | | 124 |

( 2 ) INFORMATION FOR SEQ ID NO:73:

( i ) SEQUENCE CHARACTERISTICS:
        ( A ) LENGTH: 263 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
   ( A ) NAME/KEY: misc_feature
   ( B ) LOCATION: 1..263
   ( D ) OTHER INFORMATION: /standard_name="DB#220"

( x i ) SEQUENCE DESCRIPTION: SEQ ID NO:73:

| | | | | | |
|---|---|---|---|---|---|
| GAGATGGTGT | TTGCTAAGGG | AGACCCCGGC | ATTGCTGCTT | TATACGACAA | GCTTCTGGTT | 60 |
| TCTGAAGATT | TGTGGTCCTT | CGGTGAGCTT | TTGAGGTCTG | ACTATGAGGA | GACAAAGAGC | 120 |
| CTCCTGCTTA | AGGTTGCTGG | ACACAAGGAA | CTTCTGGAGA | ACGATCCCTC | CTTAAAACAA | 180 |
| CGATTCAGGC | TGCGTGATTC | CTATATCACT | ACTTAATGT | CTGCCAAGCT | TACACATAAA | 240 |
| GAGGATTCGT | GATCCAACTA | CAA | | | | 263 |

( 2 ) INFORMATION FOR SEQ ID NO:74:

( i ) SEQUENCE CHARACTERISTICS:
      ( A ) LENGTH: 253 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Lycopersicon esculentum cv 'Rutgers Large
         Red'

( i x ) FEATURE:
      ( A ) NAME/KEY: misc_feature
      ( B ) LOCATION: 1..253
      ( D ) OTHER INFORMATION: /standard_name="DB#221"

( x i ) SEQUENCE DESCRIPTION: SEQ ID NO:74:

| | | | | | |
|---|---|---|---|---|---|
| ACCGTGAGGG | GGATTTTTAG | GGGCCTAATT | TTGTTGGGAC | TCTGTTCCTT | GCTACTGGTC | 60 |
| GCGCCTTGGT | AATATGTAAA | AATGGCAGAC | GAAGTTTAGG | TTGAACAATG | AGGAAGCAAC | 120 |
| TTTAAACATT | TGTAGTCCCA | TTAAGCAGAG | TGGTGAGCTG | CAAATGGTAT | CTGCTATATC | 180 |
| CTATGGGGTT | TAGAGTAGAC | CAAGGTACAA | ATATAGAGCG | CCTTGATATT | GAGGCACTAA | 240 |
| TGTGTATTGA | AGT | | | | | 253 |

( 2 ) INFORMATION FOR SEQ ID NO:75:

( i ) SEQUENCE CHARACTERISTICS:
      ( A ) LENGTH: 196 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Lycopersicon esculentum cv 'Rutgers Large
         Red'

( i x ) FEATURE:
      ( A ) NAME/KEY: misc_feature
      ( B ) LOCATION: 1..196
      ( D ) OTHER INFORMATION: /standard_name="DB#222"

( x i ) SEQUENCE DESCRIPTION: SEQ ID NO:75:

| | | | | | |
|---|---|---|---|---|---|
| GGGGGGCCTC | TTTTGTAAAC | TTATCTGTGA | GCAGTGACCA | ACGTCTCTAT | AAACCTCAAT | 60 |
| CCATCAAATC | TGGGCGCAAA | TTTATCTGTA | GATGTTGATG | CTTTCACCGA | TTTTGAACAA | 120 |
| TCTTCACCAG | TTTTCTTCAA | ATTATCGTCC | TTGTGAAGAG | AAATTCGAAC | TTTGGATACA | 180 |
| GAAGAGACGG | TGACCG | | | | | 196 |

( 2 ) INFORMATION FOR SEQ ID NO:76:

( i ) SEQUENCE CHARACTERISTICS:
        ( A ) LENGTH: 148 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..148
        ( D ) OTHER INFORMATION: /standard_name="DB#223"

( x i ) SEQUENCE DESCRIPTION: SEQ ID NO:76:

```
ATCCCACTTA  GGCTGATAAA  GAAATATTAG  GGGTAGAGAA  TATTCCAGTA  TTAATTAAAT      60

TGACTCTACC  AATAAGCTTA  AGAAAGTCGC  TAATTATGAC  TGCTCAAAGT  TCCTAAGACA     120

AGTCCAGGTG  AAGGATTTCT  TATGCAAG                                          148
```

( 2 ) INFORMATION FOR SEQ ID NO:77:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..99
        ( D ) OTHER INFORMATION: /standard_name="DB#224"

( x i ) SEQUENCE DESCRIPTION: SEQ ID NO:77:

```
GAGTTATGAA  CTTACTTTAT  GATATTCAAA  TACGAACAAG  CTAAAAATAT  GTTTAGCTTT      60

ATTTTCAGGA  CATAAGAGTC  ATACATCGTT  CAGCGCTTG                               99
```

( 2 ) INFORMATION FOR SEQ ID NO:78:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..226
        ( D ) OTHER INFORMATION: /standard_name="DB#226"

( x i ) SEQUENCE DESCRIPTION: SEQ ID NO:78:

```
AAGAAAGAAA  AAAAGAGGTG  AAGAAATTGT  AAGAAAAACT  GTTGTTACAA  GGAAATGTCA      60

CTTCACCATT  AAAATTTTGG  AAAAAACATG  GACACAATCC  CTTTCAATGG  GTGGTGCTTC     120
```

| | | | | | |
|---|---|---|---|---|---|
| AAGATATAAC | ATAACGAAGT | TAAAGAAATA | GATGAGAGGG | GGGAAAGACA | ACACAAGACA | 180
| ATGTTTTCCC | CCTTTATATT | AAAAGACATG | TTTTTTTGTT | TTATGT | | 226

( 2 ) INFORMATION FOR SEQ ID NO:79:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..276
        ( D ) OTHER INFORMATION: /standard_name="DB#227"

( x i ) SEQUENCE DESCRIPTION: SEQ ID NO:79:

| | | | | | |
|---|---|---|---|---|---|
| CACATGCTGG | CAAGGGTATA | TTAGCACGTC | CATCACTGAT | GGTCCTGGAT | GCTTGATGTT | 60
| GCGCTGTCCT | GCTCCAGGGT | GTGATTATGC | AGTTGACTAT | ATTGTTGGTA | GTGGAAGCTA | 120
| TGATGTTACT | TGTGGGTGCT | CATATAGTTT | CTGCTGGAAT | TGTACCGAGG | AACTCATCGC | 180
| CCAGTTGATT | GTGGAACTGT | GTCTAGTGGA | TTTGAAGAAC | AGTGCAGAGT | CTGAGAACAT | 240
| GAACTGATAT | TAGCTAATTC | TAAGCCTTGT | CCGAAT | | | 276

( 2 ) INFORMATION FOR SEQ ID NO:80:

( i ) SEQUENCE CHARACTERISTICS:
        ( A ) LENGTH: 245 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..245
        ( D ) OTHER INFORMATION: /standard_name="DB#228"

( x i ) SEQUENCE DESCRIPTION: SEQ ID NO:80:

| | | | | | |
|---|---|---|---|---|---|
| GGTGCAGTTA | CTCTATCTTT | GCTATAGCCT | GGTTGTCATA | AAGTTGTGGT | GCATACAAAA | 60
| GTTTGGATAG | TTTCCAAAGA | TGTGAAGATG | ATTAACTATT | TTATCACTTT | GTAGGAGTGG | 120
| AAAAGGGCTC | GAAGGACCCA | CAGAGGGAGA | AAGTGGGGAA | AATAACTATT | GATCAATTGA | 180
| AGGTAATTGC | TCAAGAGAAG | TTGCCGGATC | TTAATTGTTC | TACTATTGAA | TCTGCAATGA | 240
| GGATA | | | | | | 245

( 2 ) INFORMATION FOR SEQ ID NO:81:

( i ) SEQUENCE CHARACTERISTICS:
        ( A ) LENGTH: 233 base pairs
        ( B ) TYPE: nucleic acid
        ( C ) STRANDEDNESS: single
        ( D ) TOPOLOGY: linear ( i i ) MOLECULE TYPE: DNA (genomic)

5,612,471

85

-continued

86

(vi) ORIGINAL SOURCE:
  (A) ORGANISM: Lycopersicon esculentum cv 'Rutgers Large
    Red'

(ix) FEATURE:
  (A) NAME/KEY: misc_feature
  (B) LOCATION: 1..233
  (D) OTHER INFORMATION: /standard_name="DB#230"

(xi) SEQUENCE DESCRIPTION: SEQ ID NO:81:

| | | | | | |
|---|---|---|---|---|---|
| AAGCCAAGTT | TCTATGACCA | GAAGCAGTCA | CATACAAGTC | CATGCTCAGT | AATTATAGAA | 60
| GCAGTCACAT | ACAAGTCCAT | GCTCAGTAAT | TATAACTGTT | TCGCCACATC | AAAATTCAAT | 120
| ATCTATCATA | TAGAGCTGTG | CCAAAGGCAA | ATAAACATAA | CTGTTTTTGC | CCAAGCTAAA | 180
| TCTAACGTAA | CGACTTTCAA | TTGCCTCGTA | TTGGGATCTG | CCATCACATA | ATG | 233

(2) INFORMATION FOR SEQ ID NO:82:

(i) SEQUENCE CHARACTERISTICS:
    (A) LENGTH: 174 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Lycopersicon esculentum cv 'Rutgers Large
      Red'

(ix) FEATURE:
    (A) NAME/KEY: misc_feature
    (B) LOCATION: 1..174
    (D) OTHER INFORMATION: /standard_name="DB#231"

(xi) SEQUENCE DESCRIPTION: SEQ ID NO:82:

| | | | | | |
|---|---|---|---|---|---|
| CGGGACCACA | GAAACACAAC | ACACACCGGA | TACAGAGAAA | CAAGGACCGG | CATTGTCTTC | 60
| TGTAGGACAG | ACACAACGAC | TTCAACCAAG | TTCCACAGAA | ACTAGGACCC | GGACTCAAAC | 120
| AAAACCTTCA | CCGTAAAGTT | CCACACGTTA | AACAACAATA | TCCACCCTAA | GAGT | 174

(2) INFORMATION FOR SEQ ID NO:83:

(i) SEQUENCE CHARACTERISTICS:
    (A) LENGTH: 287 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Lycopersicon esculentum cv 'Rutgers Large
      Red'

(ix) FEATURE:
    (A) NAME/KEY: misc_feature
    (B) LOCATION: 1..287
    (D) OTHER INFORMATION: /standard_name="DB#232"

(xi) SEQUENCE DESCRIPTION: SEQ ID NO:83:

| | | | | | |
|---|---|---|---|---|---|
| AAGAGAACGA | AACGCACGTA | ATGGTTATCA | TAGCTTTCCA | CAATTTCACA | TTAACCAAAA | 60
| CAATTGCACT | ACTTGTAGGC | TAATGAACTG | GTGATGGTTG | AGAAACTGGA | GATGTTTATT | 120
| AGTGAAGGAA | AAACACAGAA | CAGGTTTAAA | CACACTGGAA | ACATAAATAA | CAGAAGACTG | 180
| CTGCAGAAGT | CACACTGAAC | TCATACCAAA | GACCATTTCA | ACTGCTACAT | TAGACTAGAA | 240
| GAGACCTTCC | ATGACTGCCA | CAGCTTCCTC | TCAGCATACC | TCTGCTC | | 287

( 2 ) INFORMATION FOR SEQ ID NO:84:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..277
        ( D ) OTHER INFORMATION: /standard_name="DB#233"

( x i ) SEQUENCE DESCRIPTION: SEQ ID NO:84:

| | | | | | |
|---|---|---|---|---|---|
| ACCCATCAAA | AAGTGTATTT | ATACTCTCAG | TGCACATATG | TTCAGCACTC | GTGCTGTCTG | 60 |
| ATCTAGGGCC | AAAACTGCGC | ACAGGTCACA | ACCTGCAATC | ACCTCATTAC | ACATTTGAGA | 120 |
| AATGAGCAAA | ATAATACTTC | CACATTCAGC | ATAAACAAA | AGTTCATCTG | ACGTTGAATC | 180 |
| TGTTTAAGAA | TGAGATGATG | AATCTGTTTT | CTCAGCCAAA | TAGTGCTCAA | GCATATCTCT | 240 |
| CATCATCATC | TCACTCATCA | CTCGAATCAT | ATCATCC | | | 277 |

( 2 ) INFORMATION FOR SEQ ID NO:85:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..255
        ( D ) OTHER INFORMATION: /standard_name="DB#234"

( x i ) SEQUENCE DESCRIPTION: SEQ ID NO:85:

| | | | | | |
|---|---|---|---|---|---|
| GTGGCCCTCA | ACTAAGTTGG | CCAATTTATT | GGATCATTTT | AATTAACTAA | TAACTGAAAT | 60 |
| ATCAGAGAGA | CAACGTTCCT | CATATCTGCA | AGAAGCTAAA | AAGGCGGCAA | CGTCGGTGCC | 120 |
| CTTACATGTA | TGTGCTGCAC | GACCTTAAAA | AGTCAAATT | TGAAAGAAGA | TGATCTTCCT | 180 |
| ACATATTTAC | ACTGTTTGTA | GCAAAGAAC | ACCGCAAAAG | AAAAATCCTG | TCTCATCATC | 240 |
| GACAAGCAGG | TGCCA | | | | | 255 |

( 2 ) INFORMATION FOR SEQ ID NO:86:

( i ) SEQUENCE CHARACTERISTICS:
        ( A ) LENGTH: 202 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature (B) LOCATION: 1..202
(D) OTHER INFORMATION: /standard_name="DB#236"

(xi) SEQUENCE DESCRIPTION: SEQ ID NO:86:

| | | | | | |
|---|---|---|---|---|---|
| GAGAAGGGGG | AAAGGGGGAG | CTCGGAGGGA | GGGTGAGGAA | ATGTTTACAC | CCTCTCCCCC | 60
| GCATGCTGAG | GTCCCTCCAC | CAACTTAAGG | AAGCAAAATT | ACTACAGCAA | ATTTCTGAAA | 120
| TTTAGCAAAG | AGGAACAAAA | CAATTGCAAC | CACTGATTTC | CTGCTTGTCT | GCTTGGCCGG | 180
| GTGTGCGTCG | CCGTGTTGGG | CT | | | | 202

(2) INFORMATION FOR SEQ ID NO:87:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..77
        (D) OTHER INFORMATION: /standard_name="DB#239"

(xi) SEQUENCE DESCRIPTION: SEQ ID NO:87:

| | | | | | |
|---|---|---|---|---|---|
| AGTGAAGGCG | GCGGCGGCGG | CAGAGGAGGT | ATGATTATTT | TGGTGTTTAG | AGGGCATGGA | 60
| GGGTCACGTG | TAGCGAA | | | | | 77

(2) INFORMATION FOR SEQ ID NO:88:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..222
        (D) OTHER INFORMATION: /standard_name="DB#240"

(xi) SEQUENCE DESCRIPTION: SEQ ID NO:88:

| | | | | | |
|---|---|---|---|---|---|
| AAAGCAACAC | AAACCTCTTC | ATTTCATCTG | GCAAAAAGT | ACAATCAATC | ACTCAAAATT | 60
| GACTTATAAC | TCATAACAGT | AGGAATCCTA | AATAGATGGG | AAATTAACAG | AAGCATTATT | 120
| CAATGAACTG | ACAAAGACAA | TATGTCATCA | TGTAAGGTCT | AATGAACCAA | AAATGCAATG | 180
| CTGATATGGA | AATGAAATTA | GTAGATTGAG | ATCTTCTCGC | AG | | 222

(2) INFORMATION FOR SEQ ID NO:89:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: DNA (genomic)

( v i ) ORIGINAL SOURCE:
    ( A ) ORGANISM: Lycopersicon esculentum cv 'Rutgers Large
        Red'

( i x ) FEATURE:
    ( A ) NAME/KEY: misc_feature
    ( B ) LOCATION: 1..309
    ( D ) OTHER INFORMATION: /standard_name="DB#241"

( x i ) SEQUENCE DESCRIPTION: SEQ ID NO:89:

| | | | | | | |
|---|---|---|---|---|---|---|
| CCAAGATACT | GATTACTGTT | TTCTGTTGAA | CCGGCATGTC | TGTATCTTGT | GTATATAGTT | 60 |
| TAATTCTGGA | GCATGATGGC | TAAAATGAGA | TCTTGATAAC | TAGGCATAGT | AATTGATAAA | 120 |
| TGTGTGTCTT | TAAGCATGAT | ATAGAGGTAC | ACCACAGCAT | TACCCTAAGT | CTAAAATTCA | 180 |
| AACTAGGTGT | CTAATAATCT | GGTAGAGTGA | TGAGAGTTCA | AGTGAGTGTG | AGGAAGATTT | 240 |
| GAATAGTCCA | TATTTGTACT | GAGCTAGAAC | TTGGCTGATC | CTGAGCCTGT | ATTACGCTAA | 300 |
| GAAGTCCTA  |            |            |            |            |            | 309 |

( 2 ) INFORMATION FOR SEQ ID NO:90:

( i ) SEQUENCE CHARACTERISTICS:
        ( A ) LENGTH: 246 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..246
        ( D ) OTHER INFORMATION: /standard_name="DB#244"

( x i ) SEQUENCE DESCRIPTION: SEQ ID NO:90:

| | | | | | | |
|---|---|---|---|---|---|---|
| AGAAGTGCTG | GAGGCCCTTC | TTCTGCAACA | ATAGTCTTCA | CACAATCAAC | AATGCTCTTG | 60 |
| TATTGATTGG | CAGAACCCTG | AGTCATTAAT | CTCGTCTTAA | TGACATCAAG | AGGAGTAGTT | 120 |
| ATAGCTCCAG | TTAGAGCACC | AGCAAAAGCA | CCGATAACTG | CATTCTCTGG | ATCATTCAAT | 180 |
| TCCCTTTTTG | CAGCCAGCTT | ATAACCTATC | CGCAGCTGCT | CATAGTAACG | ACTGGATGGC | 240 |
| ATCAAC     |            |            |            |            |            | 246 |

( 2 ) INFORMATION FOR SEQ ID NO:91:

( i ) SEQUENCE CHARACTERISTICS:
        ( A ) LENGTH: 205 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..205
        ( D ) OTHER INFORMATION: /standard_name="DB#246"

( x i ) SEQUENCE DESCRIPTION: SEQ ID NO:91:

| | | | | | | |
|---|---|---|---|---|---|---|
| GCGGAGGAGA | ACATCTCCGT | GTTGCTGAAG | TTTGCCTTCC | AGGTCGTCTA | TTTTCGACGT | 60 |
| TGGTGGTTGG | ATCACGCGTC | CGTCGGAGCT | CGGAGGTTTC | ACCTGAGACG | ACGTCGCCGC | 120 |

```
AGCTGGCTTT  GCGGTTGTTT  CTCCACGAGT  TCACTGGGAC  TGTTTGGTTG  CTCACCGAGA      180

GCTCGTGCTT  TGTTGTTGTT  GTTGC                                               205
```

( 2 ) INFORMATION FOR SEQ ID NO:92:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..107
        ( D ) OTHER INFORMATION: /standard_name="DB#247"

( x i ) SEQUENCE DESCRIPTION: SEQ ID NO:92:

```
GGCGGCGTTG  TGAAGCCTTA  TCATGCTTAT  ACGCCATCTG  GGTAGCGTAT  GGTGAGCCTT      60

TTTTTTGAAG  TTATGGGAAG  GAAAAGGACT  ATATTCCCCT  TGGTCGA                    107
```

( 2 ) INFORMATION FOR SEQ ID NO:93:

( i ) SEQUENCE CHARACTERISTICS:
        ( A ) LENGTH: 209 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..209
        ( D ) OTHER INFORMATION: /standard_name="DB#249"

( x i ) SEQUENCE DESCRIPTION: SEQ ID NO:93:

```
AGACCCACAA  ATCAAACTCA  AACAAATTCA  ATTTAGAACT  CATTGGATAA  AGGAGCATGT      60

TCTTGTGTCA  TGAACACATT  TGTGTAAATA  AGACCAGCCA  AACTACCACC  AACTAATGGA     120

CCAATCCAGT  AGATCCAGAA  ACCCTCAAAG  TTACCACTAA  CCATTGCAGG  TCCAAATGAA     180

CGAGCTGGGT  TCATTGATCC  ACCGGAGAA                                         209
```

( 2 ) INFORMATION FOR SEQ ID NO:94:

( i ) SEQUENCE CHARACTERISTICS:
        ( A ) LENGTH: 199 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..199
        ( D ) OTHER INFORMATION: /standard_name="DB#250"

( x i ) SEQUENCE DESCRIPTION: SEQ ID NO:94:

| | | | | | |
|---|---|---|---|---|---|
| CTCACATATC | AATGATTTTC | TAGCGGACGG | CAAAATCCTT | ACAAGTCTAG | AAACTCAATG | 60
| ATGTGTAAAG | GCTCAATCCA | TGCGAGCAGA | ATAAACCCT | AGATACCATA | GAGGGAGAGG | 120
| AGGAAAACGG | AGAAAGCAGT | GGTGGGACGA | AGCTTACTGG | ATTGGAATGT | GTGTAGGTGG | 180
| AGTGATGGAT | GGACCTGAA | | | | | 199

( 2 ) INFORMATION FOR SEQ ID NO:95:

( i ) SEQUENCE CHARACTERISTICS:
        ( A ) LENGTH: 211 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..211
        ( D ) OTHER INFORMATION: /standard_name="DB#252"

( x i ) SEQUENCE DESCRIPTION: SEQ ID NO:95:

| | | | | | |
|---|---|---|---|---|---|
| AATTAATAAA | TCTCCATTCA | TTTCCATTCA | AGAGAACTTT | GTAAACAAGG | ATCCACAGGG | 60
| TAACATCACG | GTAACAATAG | AGGTCAAAAG | CAGAACACTA | ACAGTAACCA | GGGCAAAACC | 120
| ATAAACGTAA | CTTCATCAAC | ACTTCGAAAC | CATAAGTAAG | TTCAGACGAG | ACCAATCTAA | 180
| AAAGCCAACA | GAAAATCTAA | TCCTTATCGG | C | | | 211

( 2 ) INFORMATION FOR SEQ ID NO:96:

( i ) SEQUENCE CHARACTERISTICS:
        ( A ) LENGTH: 203 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large Red'

( i x ) FEATURE:
        ( A ) NAME/KEY: misc_feature
        ( B ) LOCATION: 1..203
        ( D ) OTHER INFORMATION: /standard_name="DB#255"

( x i ) SEQUENCE DESCRIPTION: SEQ ID NO:96:

| | | | | | |
|---|---|---|---|---|---|
| TGAATATGAT | GGCCCTCGTA | AGATTTAATA | TGAATTGAGC | CTTTGGAGTT | TGAATATGAA | 60
| TGATGATCTT | GGCGATTTGA | ATATGAATGG | CCCTTTGGCG | TCTTGAATGG | CAATGGCCTT | 120
| TTGGCATTTG | AATATGATGA | CCTTGGCAGC | TTGATATATG | CTTTGGCATT | TATATGATGC | 180
| TTTGGCAGTT | TGAGTAGCGG | CCG | | | | 203

( 2 ) INFORMATION FOR SEQ ID NO:97:

( i ) SEQUENCE CHARACTERISTICS:
        ( A ) LENGTH: 184 base pairs
        ( B ) TYPE: nucleic acid
        ( C ) STRANDEDNESS: single
        ( D ) TOPOLOGY: linear (ii) MOLECULE TYPE: DNA (genomic)

(vi) ORIGINAL SOURCE:
    (A) ORGANISM: Lycopersicon esculentum cv 'Rutgers Large Red'

(ix) FEATURE:
    (A) NAME/KEY: misc_feature
    (B) LOCATION: 1..184
    (D) OTHER INFORMATION: /standard_name="DB#256"

(xi) SEQUENCE DESCRIPTION: SEQ ID NO:97:

```
CCCTATCACT CAGATTGCTA AAAAAAAAC ACTTCCATTT GCAGCATCTG ATTACCACAA        60
TTTTTCCTGG TAATTCAAAA AAAAAAACC ATACTATTAC ATTAAAGGAC GAACCTTTTA      120
GTTGAAATAA TTGTCACCAC GAATATGAAA CTGGACTTCT AACTTGGTTT TGAGCATTGT     180
TACC                                                                  184
```

(2) INFORMATION FOR SEQ ID NO:98:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..188
        (D) OTHER INFORMATION: /standard_name="DB#263"

(xi) SEQUENCE DESCRIPTION: SEQ ID NO:98:

```
AGGGTCGCAT GTTGGTAAGG AGCCACAGAA GTTTATTGAT GAGGTCAATA AAATATTTGG      60
TATGATGTCA ATAACTGCGT CGTTATAGGT GAGATTGGCA TCCTCCAAAC TCAAGGATCG    120
TGACGCACAT AGGTTTACTC AGTGGAAAGA CACAACATGA TTTTGGAGAA CTCAGTAAGC    180
GGCCGCAT                                                             188
```

(2) INFORMATION FOR SEQ ID NO:99:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lycopersicon esculentum cv 'Rutgers Large Red'

(ix) FEATURE:
        (A) NAME/KEY: misc_feature
        (B) LOCATION: 1..193
        (D) OTHER INFORMATION: /standard_name="DB#264"

(xi) SEQUENCE DESCRIPTION: SEQ ID NO:99:

```
GTTGAGGATC TGAATCAACC TCGTCAAATG CTCGTGGAGA TGCTTTGTGA AGAACGCGGT      60
CTATTTCTGG AAATAGCTGA CATAATAATA GGATTGGGCT TGACCATCTT AAAAGGGGTT    120
ATGGAAACGA GGAACGACAA AATATGGGCG AAATTCGCTT AGAGGCAAAT AGAGACTACG    180
AGATGAATAT TCA                                                       193
```

( 2 ) INFORMATION FOR SEQ ID NO:100:

( i ) SEQUENCE CHARACTERISTICS:
        ( A ) LENGTH: 218 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..218
        ( D ) OTHER INFORMATION: /standard_name="DB#265"

( x i ) SEQUENCE DESCRIPTION: SEQ ID NO:100:

```
GGATGCTGAT  CTTGGTGGGG  ATGTTGACTC  GAGCAAGAGT  ACGTCCGGGT  ACATTACAC      60

CATAGGTGGA  AAAGCAGTAA  GTTGGATGTC  CGTGTCTTTA  GAAGTATGTT  TCTCTTTCAT    120

CCACTAAAGC  TGAGTTTGTG  GCAATAGCTG  AAGCTGGGAA  AGAGATGATA  TGGATGGCAG    180

ATTATCTTGA  GGAATTGGGC  AAGAAGCAAA  GCAGAATT                              218
```

( 2 ) INFORMATION FOR SEQ ID NO:101:

( i ) SEQUENCE CHARACTERISTICS:
        ( A ) LENGTH: 193 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..193
        ( D ) OTHER INFORMATION: /standard_name="DB#266"

( x i ) SEQUENCE DESCRIPTION: SEQ ID NO:101:

```
GGCAAACAAA  GTAGAATTAC  ATTGCAGTTT  CTCCCTTACT  AGTCATCAAA  TAAATATTCA     60

CAAATTGAAA  CACAGCTGTT  CCCTTAACAA  CCCTATGAAG  GGAGATTAAG  AAGTAACTAA    120

GTTCGTTTCA  CGGAACCTTT  ATTCATTGCA  CCCCAAGCAC  ATAGACATTG  CTGTTACAGT    180

CCAGCTGCTC  CGG                                                           193
```

( 2 ) INFORMATION FOR SEQ ID NO:102:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..131
        ( D ) OTHER INFORMATION: /standard_name="DB#275"

( x i ) SEQUENCE DESCRIPTION: SEQ ID NO:102:

| | | | | | |
|---|---|---|---|---|---|
| CAGATCATCA | ATGACCGGGA | AACTGGTAGA | TCTAGAGGAT | CTTGATGGTC | GCAACATCAC | 60
| CGTGAACGGA | GCTCAATCAC | GCGGAGGGGC | TGGAGGTGGA | GGTGGAAGAG | GCGGGGGTGG | 120
| TTAGGAGGTG | C | | | | | 131

( 2 ) INFORMATION FOR SEQ ID NO:103:

( i ) SEQUENCE CHARACTERISTICS:
        ( A ) LENGTH: 220 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..220
        ( D ) OTHER INFORMATION: /standard_name="DB#277"

( x i ) SEQUENCE DESCRIPTION: SEQ ID NO:103:

| | | | | | |
|---|---|---|---|---|---|
| GCAGTGGGCA | CATTGTTAGG | AGCAATGACA | GGAGCTTTGA | TAGGTCAAGA | AACTAAAGTG | 60
| GATTCATTAG | AGGTGCCGCG | GTTGGAGCCA | TTTCTGGTGC | TGTTTTCTCT | CTTGAGGTCT | 120
| TTGAGTCATC | TCTGATACTA | TGGCACTCTG | ATGAATCCGG | AGTTGGATGT | GTTCTGTACT | 180
| GATTGATGTA | ATAGCTAGCT | TGTTAAGTGG | TAGACTAGTT | | | 220

( 2 ) INFORMATION FOR SEQ ID NO:104:

( i ) SEQUENCE CHARACTERISTICS:
        ( A ) LENGTH: 323 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..323
        ( D ) OTHER INFORMATION: /standard_name="DB#279"

( x i ) SEQUENCE DESCRIPTION: SEQ ID NO:104:

| | | | | | |
|---|---|---|---|---|---|
| AACTAAGAAT | GCTTAGATGC | TGAAATAACC | TTGCATGTTG | AAGCAACACA | AAAACTGAAT | 60
| AAAATTTTGA | CAATGTCCTA | ATATCACAAG | GACACGAATA | GGCAAGTGAA | CATACCCATA | 120
| TCTCTAATGC | AGAGCCCTAC | TGATCCAAAT | ATGAACATGG | ACTACATGGT | TAAAAATTTT | 180
| ACACTCAGAT | GAATTAAGCA | AGTTGGCACA | GAAGAGGTTT | TGGTGCCCAA | CAGAAGAGTG | 240
| GATCTCACCA | AGAGCCGCCT | CTACCAAGGT | TTGAGGTCAC | CAACTGGCCA | GCAGTCCAGT | 300
| TTAAGGCTCT | CCCCGGCTTC | AGT | | | | 323

( 2 ) INFORMATION FOR SEQ ID NO:105:

( i ) SEQUENCE CHARACTERISTICS:
        ( A ) LENGTH: 336 base pairs
        ( B ) TYPE: nucleic acid
        ( C ) STRANDEDNESS: single ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..336
    ( D ) OTHER INFORMATION: /standard_name="DB#280"

( x i ) SEQUENCE DESCRIPTION: SEQ ID NO:105:

| | | | | | | |
|---|---|---|---|---|---|---|
| ATCTAACAGT | TGAAGGAGCA | GAAGAATTAG | AAAGCCACGG | AGGAAGAAGA | GTTTGTGGCG | 60 |
| TAGGAGTTGA | GGCATCGGCG | TGGAGGAAAC | CTCCATTAGA | AGTAGCCATA | GGTAAACCTG | 120 |
| GGACACTCCT | TTCTTTCACA | ATCTTTTCTG | CAAAGGTTTC | GAGAACGTGA | TCGTATTTTC | 180 |
| CATCGTCTAC | TGGATCACAC | CTTGTTGTTT | TCTTTCTGCT | CTCTCTGTTG | CCTTCTCTTT | 240 |
| GAAACTTCCC | ACCACTTTCC | TAATCTTTTA | GCAGTTCGAC | CTGGTACTTC | AGCTGCTATT | 300 |
| TTTCTCCATT | TGTTACCGTG | TTTGGCTTGT | AGTTGA | | | 336 |

( 2 ) INFORMATION FOR SEQ ID NO:106:

( i ) SEQUENCE CHARACTERISTICS:
    ( A ) LENGTH: 278 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..278
    ( D ) OTHER INFORMATION: /standard_name="DB#288"

( x i ) SEQUENCE DESCRIPTION: SEQ ID NO:106:

| | | | | | | |
|---|---|---|---|---|---|---|
| ACTTGAGAAA | TACTTTGTTT | AGTCTAAAAC | AGGAAAAAGT | ACAATTTGCC | TTCTGGAGAA | 60 |
| GAATAAGATC | TTTGTCTCAA | CTCACAAGCT | AATAATACTA | AACAAGCAAA | TGAAAGGGTA | 120 |
| GAAAACCTAG | CTAAAGAGCT | TCAGGAAAAC | AGATAATACA | TGCCAAACGG | CAATAATATA | 180 |
| GTATTCCAAG | TTGCGCATCA | CCCATAGCAA | CACCATGACT | TCCATTACAC | ATGACTGGAA | 240 |
| ACTTATTGGT | AACCAAAATT | ATGGGTATCA | GCGCAGCC | | | 278 |

( 2 ) INFORMATION FOR SEQ ID NO:107:

( i ) SEQUENCE CHARACTERISTICS:
    ( A ) LENGTH: 175 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Lycopersicon esculentum cv 'Rutgers Large Red'

( i x ) FEATURE:
    ( A ) NAME/KEY: misc_feature
    ( B ) LOCATION: 1..175
    ( D ) OTHER INFORMATION: /standard_name="DB#289"

( x i ) SEQUENCE DESCRIPTION: SEQ ID NO:107:

|  |  |  |  |  |  |  |
|---|---|---|---|---|---|---|
| TACTCACTAG | GAGCACAAGG | TTGAAGTTCT | ATTTATAACA | AAAATATGGA | ATAAACAGG | 60 |
| AAAGCAAAAC | TTCAAAATTC | AAAACACAAG | GCACTTCCAT | TAAAGTGCTT | TCATGAAATT | 120 |
| CTAAATTCTC | CTCAAAATTC | TAAACAGGAA | AACTAATTTA | GACTGATCCG | ATTTT |  175 |

( 2 ) INFORMATION FOR SEQ ID NO:108:

( i ) SEQUENCE CHARACTERISTICS:
        ( A ) LENGTH: 112 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..112
        ( D ) OTHER INFORMATION: /standard_name="DB#291"

( x i ) SEQUENCE DESCRIPTION: SEQ ID NO:108:

|  |  |  |  |  |  |  |
|---|---|---|---|---|---|---|
| GTGAATTTCT | AGAGCGTTGT | GAGCAAGATG | ATGGATTTCT | TGAAGGTTTT | ATGAGGAAGA | 60 |
| GTAGATGGAA | TGACGGGCAT | GCTTCCAAGT | CAGCAAAGGA | CGATGGGAAA | GA |  112 |

( 2 ) INFORMATION FOR SEQ ID NO:109:

( i ) SEQUENCE CHARACTERISTICS:
        ( A ) LENGTH: 825 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Lycopersicon esculentum cv 'Rutgers Large
            Red'

( i x ) FEATURE:
        ( A ) NAME/KEY: misc_feature
        ( B ) LOCATION: 1..825
        ( D ) OTHER INFORMATION: /standard_name="DB#L23762"

( x i ) SEQUENCE DESCRIPTION: SEQ ID NO:109:

|  |  |  |  |  |  |  |
|---|---|---|---|---|---|---|
| CTCTTCTTCC | ATTTCTTTCA | AAATTAAAGT | ATTGTTACTC | TGCTATTGGC | TCAAAACCTC | 60 |
| TGCAATCTCC | GTCTCCTTCA | ATTTCAACTC | AAGCAAATCC | ACCTCTTTCA | CTAGTTTCAT | 120 |
| CACTTTCAGA | TCAGGGTTTG | GAGTTGAAGG | TACGGGGGGC | TAATTGATGG | CGTCGAAGAG | 180 |
| GATATTGAAG | GAGCTCAAGG | ATCTGCAGAA | GGATCCCCCC | ACATCATGCA | GTGCTGGTCC | 240 |
| AGTGGCAGAG | GATATGTTCC | ATTGGCAAGC | AACAATCATG | GGGCCTACCG | ATAGCCCTTA | 300 |
| TGCTGGAGGT | GTATTTTTGG | TTTCAATTCA | TTTCCCTCCA | GATTATCCTT | TTAAGCCTCC | 360 |
| AAAGGTTGCC | TTCAGAACTA | AGGTTTTCCA | TCCCAACATC | AACAGCAATG | GAAGTATTTG | 420 |
| TCTGGATATT | CTTAAGGAGC | AGTGGAGTCC | AGCATTAACC | ATATCCAAGG | TCCTGCTGTC | 480 |
| CATCTGCTCT | CTGTTGACAG | ACCCAAACCC | AGATGATCCT | CTTGTACCTG | AAATTGCTCA | 540 |
| CATGTACAAG | ACTGACAGGG | CCAAATACGA | AACCACTGCT | CGTAGCTGGA | CTCAGAAATA | 600 |
| TGCAATGGGA | TGATGCGCAA | AATGTCTCCA | GGCATGTCTG | GGACTTTGTA | ACAGCAATGT | 660 |
| CTTATGTGCT | TGGGGTGAAT | GAATAAATTC | CGTGAAAGAA | CTTAGTTACT | TCTTAATCTC | 720 |
| CCTTCATGAG | GGTTGTTAAG | GGAACAGCTG | TTTTCAATTT | GTGAATATTT | ATTTGATGAC | 780 |

TAGTAAGGGA GAAACTGCAA TGTAATTCTA CTTTGTTTGC CAGTT 825

( 2 ) INFORMATION FOR SEQ ID NO:110:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..26
        ( D ) OTHER INFORMATION: /standard_name="P35"

( x i ) SEQUENCE DESCRIPTION: SEQ ID NO:110:

GTAAGCGGCC GCAGCGTCAG TAACTC 26

( 2 ) INFORMATION FOR SEQ ID NO:111:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligo)

( i x ) FEATURE:
        ( A ) NAME/KEY: misc_feature
        ( B ) LOCATION: 1..22
        ( D ) OTHER INFORMATION: /standard_name="P36"

( x i ) SEQUENCE DESCRIPTION: SEQ ID NO:111:

TACTGACGCT GCGGCCGCTT AC 22

( 2 ) INFORMATION FOR SEQ ID NO:112:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..35
        ( D ) OTHER INFORMATION: /standard_name="P39"

( x i ) SEQUENCE DESCRIPTION: SEQ ID NO:112:

ACTCTTGGGC CGAGTTGGCC TTTTTTTTTT TTTTT 35

( 2 ) INFORMATION FOR SEQ ID NO:113:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( A ) NAME/KEY: misc_feature
        ( B ) LOCATION: 1..24
        ( D ) OTHER INFORMATION: /standard_name="P40"

( x i ) SEQUENCE DESCRIPTION: SEQ ID NO:113:

ACTCTTGGGC CGAGTTGGCC TTTT 24

( 2 ) INFORMATION FOR SEQ ID NO:114:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (primer)

( i x ) FEATURE:
    ( A ) NAME/KEY: misc_feature
    ( B ) LOCATION: 1..18
    ( D ) OTHER INFORMATION: /standard_name="P46"

( x i ) SEQUENCE DESCRIPTION: SEQ ID NO:114:

GGCCAAGTTG GCCTTTTT 18